(12) United States Patent
Zhong et al.

(10) Patent No.: US 7,829,140 B1
(45) Date of Patent: Nov. 9, 2010

(54) METHOD OF FORMING IRON OXIDE CORE METAL SHELL NANOPARTICLES

(75) Inventors: Chuan-Jian Zhong, Endwell, NY (US); Lingyan Wang, Binghamton, NY (US); Jin Luo, Vestal, NY (US)

(73) Assignee: The Research Foundation of the State University of New York, Binghamton, NY (US)

(*) Notice: Subject to any disclaimer, the term of this patent is extended or adjusted under 35 U.S.C. 154(b) by 1180 days.

(21) Appl. No.: 11/391,883

(22) Filed: Mar. 29, 2006

(51) Int. Cl.
B05D 7/00 (2006.01)
(52) U.S. Cl. ...................................... 427/212
(58) Field of Classification Search ............ 427/212
See application file for complete search history.

(56) References Cited

U.S. PATENT DOCUMENTS

| | | | |
|---|---|---|---|
| 3,239,382 A | 3/1966 | Thompson | |
| 3,923,612 A | 12/1975 | Wiesner | |
| 4,554,088 A | 11/1985 | Whitehead et al. | |
| 5,132,193 A | 7/1992 | Reddy et al. | |
| 5,560,960 A | 10/1996 | Singh et al. | |
| 5,585,020 A | 12/1996 | Becker et al. | |
| 5,641,723 A | 6/1997 | Bonnemann et al. | |
| 5,789,337 A | 8/1998 | Haruta et al. | |
| 5,876,867 A | 3/1999 | Itoh et al. | |
| 5,985,232 A | 11/1999 | Howard et al. | |
| 6,162,411 A | 12/2000 | Howard et al. | |
| 6,162,532 A | 12/2000 | Black | |
| 6,180,222 B1 | 1/2001 | Schulz et al. | |
| 6,221,673 B1 | 4/2001 | Snow et al. | |
| 6,251,303 B1 | 6/2001 | Bawendi et al. | |
| 6,252,014 B1 | 6/2001 | Knauss | |

(Continued)

FOREIGN PATENT DOCUMENTS

EP 0 557 674 A1 9/1993

(Continued)

OTHER PUBLICATIONS

Wang et al., "Monodispersed Core-Shell Fe3O4@Au Nanoparticles," J. Phys. Chem. B, 109, pp. 21593-21601 (2005).*

(Continued)

*Primary Examiner*—Michael Cleveland
*Assistant Examiner*—Robert Vetere
(74) *Attorney, Agent, or Firm*—Nixon Peabody LLP

(57) ABSTRACT

A method of forming mono-disperse iron-oxide core metal shell nanoparticles is disclosed. Particle size of the oxide core seeds is controlled and capped seeds are formed. The capping layer is desorbed by a thermally activated process and metal such as gold is chemically deposited on the core seeds in situ. This process can be repeated to produce multi-metal or different metal shells. A second capping layer is applied on the core/shell composite nanoparticles. In another step, the particles are sized by centrifuging to obtain a tightly controlled and narrow particle size distribution. The water-dispersibility of the particles is achieved by a thiol exchange reaction on the gold shell of the core/shell nanoparticles or by deposition of gold on ferritin-derived iron oxide cores in aqueous solution. Mono and multilayer thin films are assembled on different substrates using the core/shell particles and linking molecules.

29 Claims, 30 Drawing Sheets

U.S. PATENT DOCUMENTS

| | | | |
|---|---|---|---|
| 6,254,662 | B1 | 7/2001 | Murray et al. |
| 6,262,129 | B1 | 7/2001 | Murray et al. |
| 6,322,901 | B1 | 11/2001 | Bawendi et al. |
| 6,344,272 | B1 | 2/2002 | Oldenburg et al. |
| 6,361,944 | B1 | 3/2002 | Mirkin et al. |
| 6,383,500 | B1 | 5/2002 | Wooley et al. |
| 6,562,403 | B2 | 5/2003 | Klabunde et al. |
| 6,773,823 | B2 | 8/2004 | O'Connor |
| 6,818,199 | B1 | 11/2004 | Hainfeld et al. |
| 6,861,387 | B2 | 3/2005 | Ruth et al. |
| 6,872,971 | B2 | 3/2005 | Hutchinson et al. |
| 6,962,685 | B2 * | 11/2005 | Sun .............................. 423/632 |
| 6,972,046 | B2 | 12/2005 | Sun et al. |
| 6,984,265 | B1 | 1/2006 | Raguse et al. |
| 7,053,021 | B1 | 5/2006 | Zhong et al. |
| 7,208,439 | B2 | 4/2007 | Zhong et al. |
| 2002/0034675 | A1 | 3/2002 | Starz et al. |
| 2002/0160195 | A1 | 10/2002 | Halas et al. |
| 2002/0174743 | A1 | 11/2002 | Mukherjee et al. |
| 2002/0194958 | A1 | 12/2002 | Lee et al. |
| 2003/0004054 | A1 | 1/2003 | Ito |
| 2003/0029274 | A1 | 2/2003 | Natan et al. |
| 2003/0166294 | A1 | 9/2003 | Kirby |
| 2004/0055419 | A1 | 3/2004 | Kurihara et al. |
| 2004/0115345 | A1 | 6/2004 | Huang et al. |
| 2004/0167257 | A1 | 8/2004 | Ryang |
| 2004/0247924 | A1 | 12/2004 | Andres |
| 2004/0261574 | A1 | 12/2004 | Lin et al. |
| 2005/0025969 | A1 | 2/2005 | Berning |
| 2005/0191231 | A1 | 9/2005 | Sun |
| 2005/0202244 | A1 | 9/2005 | Papagianakis |
| 2006/0286379 | A1 * | 12/2006 | Gao .............................. 428/403 |

FOREIGN PATENT DOCUMENTS

| | | |
|---|---|---|
| JP | 6-271905 A | 9/1994 |

OTHER PUBLICATIONS

Brust et al., "Synthesis of Thiol-Derivatised Gold Nanoparticles in a Two-Phase Liquid System," *J. Chem. Sol., Chem. Commun.* pp. 801-2 (1994).

Buffat et al., "Size Effect on the Melting Temperature of Gold Particles," *Physical Review A* 13(6):2287-98 (1976).

Carotenuto et al., "Size-Controlled Synthesis of Thiol-Derivatized Gold Clusters," *J. Mater. Chem.* 13(5)1038-41 (2003).

Chen & Sommers, "Alkanethiolate-Protected Copper Nanoparticles: Spectroscopy, Electrochemistry, and Solid-State Morphological Evolution," *J. Phys. Chem.* 105(37):8816-20 (2001).

Clarke et al., "Size-Dependent Solubility of Thiol-Derivatized Gold Nanoparticles in Supercritical Ethane," *Langmuir* 17(20):6048-50 (2001).

Daniel & Astruc, "Gold Nanoparticles: Assembly, Supramolecular Chemistry, Quantum-Size-Related Properties, and Applications Toward Biology, Catalysis, and Nanotechnology," *Chem. Rev.* 104(1):293-346 (2004).

Fan et al., "Ordered Nanocrystal/Silica Particles Self-assembled from Nanocrystal Micelles and Silicate," *Chem. Commun.* 2323-5 (2006).

Han et al., "Core-Shell nanostructured Nanoparticle Films as Chemically Sensitive Interfaces," *Anal. Chem.* 73:4441-9 (2001).

Han et al., "Nanoparticle-Structured Sensing Array Materials and Pattern Recognition for VOC Detection," *Sensors and Actuators B* 106:431-41 (2005).

Han et al., "Quartz-Crystal Microbalance and Spectrophotometric Assessments of Inter-Core and Inter-Shell Reactivities in Nanoparticle Thin Film Formation and Growth," *Journal of Materials Chemistry* 11:1258-64 (2001).

Haruta, "Size- and Support-dependency in the Catalysis of Gold," *Catalysis Today* 36:153-166 (1997).

Hostetler et al., "Stable, Monolayer-Protected Metal Alloy Clusters," *J. Am. Chem. Soc.* 120:9396-7 (1998).

Hu et al., "Competitive Photochemical Reactivity in a Self-Assembled Monolayer on a Colloidal Gold Cluster," *J. Am. Chem. Soc.* 123:1464-70 (2001).

Hussain et al., "Preparation of Acrylate-Stabilized Gold and Silver Hydrosols and Gold-Polymer Composite Films," *Lanmuir* 19:4831-5 (2003).

Ito et al., "Medical Application of Functionalized Magnetic Nanoparticles," *J. Biosci. Bioeng.* 100(1):1-11 (2005).

Jana et al., "Seeding Growth for Size Control of 5-40 nm Diameter Gold Nanoparticles," *Langmuir* 17:6782-6 (2001).

Kim et al., "Particle Size Control of 11-Mercaptoundecanoic Acid-Protected Au Nanoparticles by Using Heat-Treatment Method," *Chem. Letters* 33(3):344-5 (2004).

Leibowitz et al., "Structures and Properties of Nanoparticle Thin Films Formed via a One-Step Exchange—Cross-Linking—Precipitation Route," *Anal. Chem.* 71(22):5076-83 (1999).

Lewis et al., "Melting, Freezing, and Coalescence of Gold Nanoclusters," *Physicl Review B* 56(4):2248-57 (1997).

Lou et al., "Gold platinum Alloy Nanoparticle Assembly as Catalyst for Methanol Electrooxidation," *Chem. Commun.* 473-474 (2001).

Lu et al., "Magnetic Nanoparticles: Synthesis, Protection, Functionalization, and Application," *Angew. Chem. Int. Ed.* 46:1222-44 (2007).

Luo et al., "AFM Probing of Thermal Activation of Molecularly Linked Nanoparticle Assembly," *J. Phys. Chem.* 108(28):9669-77 (2004).

Luo et al., "An EQCN Assessment of Electrocatalytic Oxidation of Methanol at Nanostructured Au-Pt Alloy Nanoparticles," *Electrochemistry Communications* 3:172-6 (2001).

Luo et al., "Thermal Activation of Molecularly-Wired Gold Nanoparticles on a Substrate as Catalyst," *Journal of American Chemical Society* 124:13988-9 (2002).

Maye et al., "Core-Shell Gold Nanoparticle Assembly as Novel Electrocatalyst of CO Oxidation," *Langmuir* 16(19):7520-7523 (2000).

Maye et al., "Heating-Induced Evolution of Thiloate-Encapsulated Gold Nanoparticles: A Strategy for Size and Shape Manipulations," *Langmuir* 16:490-7 (2000).

Maye et al., "Manipulating Core-Shell Reactivities for Processing Nanoparticle Sizes and Shapes," *J. Mater. Chem.* 10:1895-1901 (2000).

Maye et al., "Size Controlled Assembly of Gold Nanoparticles Induced by a Tridentate Thioether Ligand," *J. Am. Chem. Soc.* 125:9906-7 (2003).

Merriam Webster, New Collegiate Dictionary, G. & C. Merriam Company p. 105 (1979).

Park et al., "Fabrication of Magnetic Core@Shell Fe Oxide@Au Nanoparticles for Interfacial Bioactivity and Bio-separation," *Langmuir* 23(17):9050-6 (2007).

Paulus et al., "New PtRu Alloy Colloids as Precursors for Fuel Cell Catalysts," *Journal of Catalysts* 195:383-393 (2000).

Sau et al., "Size Controlled Synthesis of Gold Nanoparticles Using Photochemically Prepared Seed Particles," *Journal of Nanoparticle Research* 3:257-61 (2001).

Schadt et al., "Molecularly Tuned Size Selectivity in Thermal Processing of Gold Nanoparticles," *Chem. Mater.* 18(22):5147-9 (2006).

Schmid et al., "Ligand-stabilized Metal Clusters and Colloids: Properties and Applications," *J. Chem. Soc.* 5:589-595 (1996).

Shaffer et al., "Comparison Study of the Solution Phase Versus Solid Phase Place Exchange Reactions in the Controlled Functionalization of Gold Nanoparticles," *Langmuir* 20(19):8343-51 (2004).

Shimizu et al., "Size Evolution of Alkanethiol-Protected Gold Nanoparticles by Heat Treatment in the Solid State," *J. Phys. Chem. B* 107:2719-24 (2003).

Sun et al., "Monodisperse FePt Nanoparticles and Ferromagnetic FePt Nanocrystal Superlattices," *Science* 287:1989-92 (2000).

Templeton et al., "Monolayer-Protected Cluster Molecules," *Acc. Chem. Res.* 33:27-36 (2000).

Teranishi et al., "Heat-Induced Size Evolution of Gold Nanoparticles in the Solid State," *Adv. Mater.* 13(22):1699-1701 (2001).

Terzi et al., "3-Methylthiophene Self-Assembled Monolayers on Planar and Nanoparticle Au Surfaces," *J. Phys. Chem.* 109(41):19397-402 (2005).

Thomas et al., "Photochemistry of Chromophore-Functionalized Gold Nanoparticles," *Pure Appl. Chem.* 74(9):1731-8 (2002) [1190].

Wang et al., "Monodispersed Core-Shell $Fe_3O_4$@Au Nanoparticles," *J. Phys. Chem.* 109(46):21593-601 (2005).

Xia et al., "Monodispersed Colloidal Spheres: Old Materials with New Applications," *Adv. Mater.* 12:693-713 (2000).

Zhai et al., "Regioregular Polythiophene/Gold Nanoparticle Hybrid Materials," *J. Mater. Chem.* pp. 141-143 (2004).

Zhong et al., "Core-Shell Assembled Nanoparticles as Catalysts," *Adv. Mater.* 13(19):1507-11 (2001).

Zhong et al., "Electrode Nanomaterials Self-Assembled from Thiolate-Encapsulated Gold Nanocrystals," *Electrothem. Commun.* 1:72 (1999).

Zhong et al., "Size and Shape Evolution of Core-Shell Nanocrystals," *Chem. Commun.* pp. 1211-1212 (1999).

* cited by examiner

METHOD OF FORMING IRON OXIDE CORE METAL SHELL NANOPARTICLES

FUNDED RESEARCH

This invention was made with government support under CHE0349040 awarded by National Science Foundation. The government has certain rights in the invention.

FIELD OF THE INVENTION

The invention is related to mono-disperse iron oxide (Fe-Oxide) core metal shell nanoparticles, and more particularly to a method of formation thereof, as well as a method of forming thin film assemblies thereof. Some of the iron oxide-core shell nanoparticles may exhibit superparamagnetic properties.

BACKGROUND OF THE INVENTION

A core/shell nanoparticle consists of an iron oxide core fully covered by at least one metal shell. A capping layer may optionally be present on the core/shell nanoparticles. The ability to control the size and mono-dispersity in synthesizing and assembling metal-coated superparamagnetic nanoparticles is important in technological applications of the nanoscale core, shell or their combinations. Size control and mono-dispersity is increasingly important for many applications involving magnetic nanoparticles such as magnetic resonance imaging for medical diagnosis, high-density magnetic recording, controlled drug delivery, biological targeting or separation, ferrofluids and catalysis.

DESCRIPTION OF RELATED ART

Magnetic nanoparticles with controlled size dispersions have been described in U.S. PGPUB 2005/0191231 on an application to Sun. The '231 reference does not form core/metal shell nanoparticles nor does it centrifuge core/shell composites. Although the reference discloses mono-disperse iron-oxide nanoparticles, a wide range of dimensions (from 2 nm-20 nm) is obtained by the process.

It is also known to form magnetic core/metal shell nanoparticles. Fe-coated iron oxides and Pt-, Ag- or Au-coated iron oxides have been described. U.S. PGPUB 2005/0202244 on an application of Papagianakis teaches an iron-oxide core supporting a metal. The supported metal is primarily Fe although other metals such as Au and Pt are mentioned. Methods of forming the Au or Pt shells are not described. The core size ranges from 75 nm to 990 nm. It is not clear if the supported metal envelopes the core.

More recently, an approach has been demonstrated for the formation of gold-coated $Fe_3O_4$ nanoparticles which involves the attachment of 2 nm-3 nm sized gold nanoparticles via 3-aminopropyl triethylsilane onto 10 nm sized $Fe_3O_4$ nanoparticles. Such attachments may not fully encapsulate the magnetic core.

U.S. PGPUB 2003/0004054 on an application of Ito et al. describes metal-oxide core particles with attached Au nanoparticles used in catalysis. The core particles are oxides of Ce, Zr, and the like and are not superparamagnetic. The coating is partial and is an anti-sintering agent.

In U.S. Pat. No. 6,773,823, O'Conner et al. describe a microemulsion synthesis of a Fe/Au core/shell nanoparticle.

U.S. PGPUB 2003/0166294, on an application of Kirby et al. shows gold nanoparticles attached to iron oxide for a CO gas sensor.

In U.S. PGPUB 2004/0247924, on an application of Andres et al., a Fe/Au nanoparticle is produced in a distributed arc cluster source.

In U.S. PGPUB 2005/0025969, Berning et al. disclose gold-coated magnetic nanoparticle for use in biotechnology applications. The reducing agent is selected from the group: sodium citrate, sodium borohydride, white phosphorus, lithium aluminum hydride, and sodium cyanoborohydride.

The formation of thin films of magnetic nanoparticles has also attracted considerable interest. U.S. Pat. No. 6,162,532 to Black et al. teaches forming a thin film of uniformly sized magnetic nanoparticles.

However, none of these references teaches the art of controlling the size of the Fe-oxide core/metal shell nanoparticles or the variability in thickness of the shell. Nor are the properties of thin films with uniform sized particles disclosed.

SUMMARY OF THE INVENTION

This invention is a novel method of forming Fe-oxide core/metal shell nanoparticles with controlled sizes and tightly controlled size distributions. A method of controlling the size of the core seed by varying the process parameters is also taught. A capping layer on the core seed is thermally desorbed prior to coating the core with a metal shell such as a gold shell. A capping layer is formed on the composite core/shell nanoparticle.

The inventive method permits controlled deposition of the metal shells to desired thicknesses based on the size of the core seed. In one embodiment, the resulting nanoparticles are sized to produce core/shell nanoparticles with very narrow size distributions not achieved in the prior art. In another embodiment, the core/shell nanoparticles are made water-dispersible by ligand-exchange with the capping layer. Also disclosed are a thiol-mediated capping layer formed on the core/shell nanoparticles and the assembly of the capped nanoparticles on substrates as uniform thin films. In yet another embodiment, multiple metal shells are sequentially formed on the core to form a core/multi-shell nanoparticle composite wherein the multiple shells show unexpected synergistic effects during catalysis and adsorption reactions.

BRIEF DESCRIPTION OF THE DRAWINGS

A complete understanding of the present invention may be obtained by reference to the accompanying drawings, when considered in conjunction with the subsequent detailed description, in which.

DETAILED DESCRIPTION OF THE PREFERRED EMBODIMENT

The present invention is a method of forming an iron-oxide core/metal shell nanoparticle with optical, electrical, catalytic, or superparamagnetic properties. Multiple shell layers may be formed in sequence over the iron-oxide core.

Figure 1:
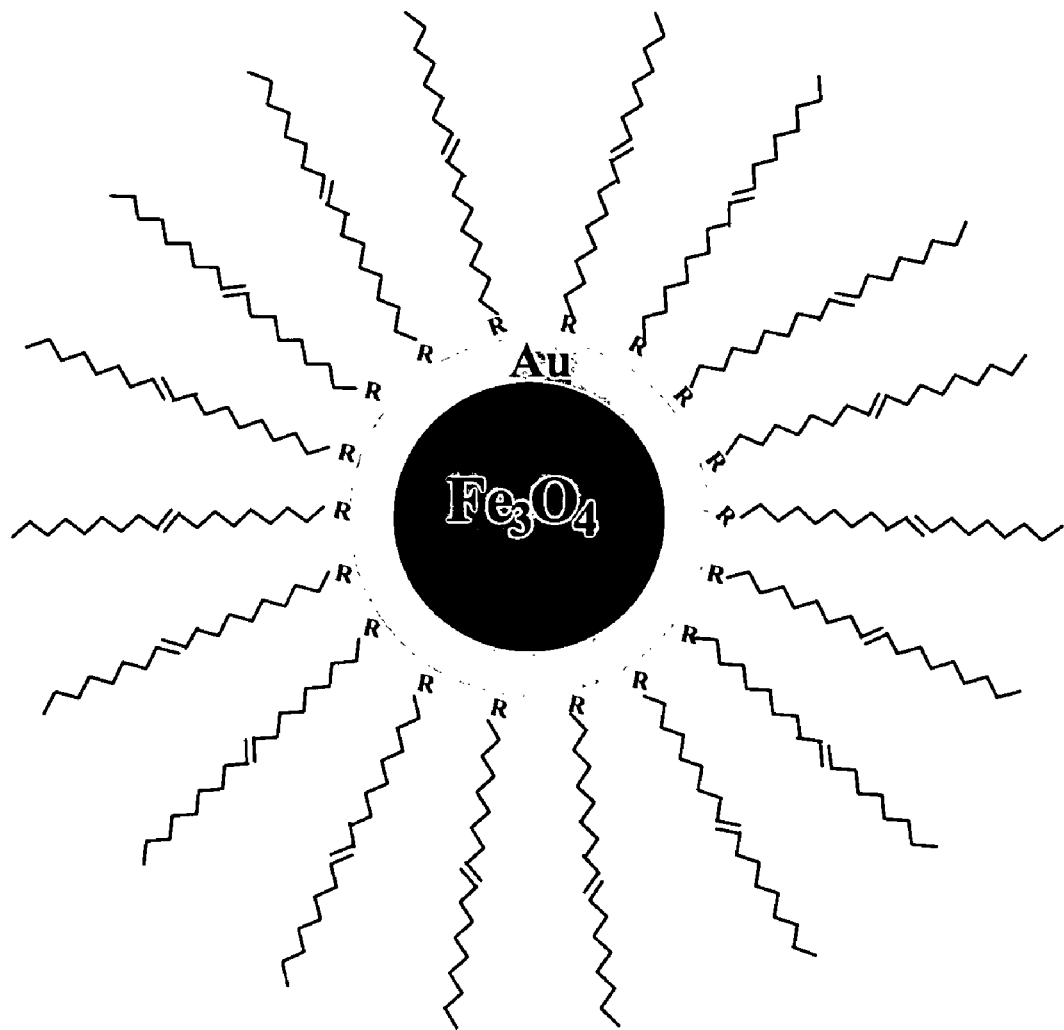
FIG. 1 shows a prior art core/shell nanoparticle.

Referring to FIG. 1, there is shown a schematic view of a conventional nanoparticle core and a shell of the prior art. A suitable precursor compound of an iron oxide is reduced or oxidized by one or more reactants in the presence of a solvent and one or more capping agents. Nano-sized core seeds of iron oxide are formed in suspension in the solvent with a capping layer. The predetermined diameter of the core seeds and their size distribution is achieved by controlling, among other factors, the reaction temperature, the molar ratio between the precursor and capping agents and the reaction time. A suitable metal precursor compound of the shell material is introduced into the suspension containing the core seeds along with a second solvent and a second capping agent. The second capping agent or agents may be the same as the first agent or agents. In this novel method of synthesis the first capping agent is thermally desorbed from the core seed prior to coating it in situ with the shell material. A predetermined coating thickness of the shell material is achieved by controlling the molar ratios of the shell and core materials in solution and the temperature and time of reaction. The second capping agent is formed on the core/shell nanoparticle.

The core/shell nanoparticles are then sized and separated once or multiple times. Diverse sizing techniques are known in the arts of magnetic separation, centrifuging, and the like. The novel sizing step results in core/shell particles with desired uniform diameters and more importantly a controlled, narrow size distribution. The mono-disperse core/shell nanoparticles may be processed further for suitable applications.

In one application, a thin film monolayer or multiple layers of the core/sell nanoparticles are assembled on a suitable substrate. The substrate is introduced into the suspension of core/shell nano material with a third capping (bifunctional) agent and subsequently withdrawn. This technique involves exchange, cross-linking, and precipitation. The second capping layer may be replaced by the third capping agent followed by crosslinking via a gold-thiolate bonding when the bifunctional agent is a dithiol linker. The mechanism would be hydrogen bonding if the bifunctional agent is a coarboxylic-acid-functionalized thiol linker. The film thickness is controlled by the concentration of the nanoparticles in suspension and the time of immersion. Since the particle size in suspension is uniform and well controlled, the thin film assembly is uniform. The interparticle spacing in the film is also predictable and uniform. Where multiple layers are present in the thin film, the film thickness would also be uniform and well controlled.

The core seed may be any iron oxide including $Fe_3O_4$, $\gamma$-$Fe_2O_3$, FeOOH, and $\alpha$-$Fe_2O_3$. The seed particle may be any shape including sphere, rod, or platelet.

The shell material may be any metal or alloy, such as Au, Ag, Pt, Cu, Ni, Pd, Au/Pt (multilayer), AuPt (alloy) and AgAu (alloy), which is selected based on the application. Noble metals coating on the core is useful for example in medical diagnostics, drug delivery, and catalyst. The innovative method is illustrated in the following examples which focus on iron-oxide cores and Au shells.

Example 1

Iron(III) acetylacetonate (Fe(acac)₃, 99.9%), 1,2-hexadecanediol ($C_{14}H_{29}CH(OH)CH_2(OH)$, 90%), oleylamine (OAM, $C_9H_{18}$=$C_9H_{17}NH_2$, 70%), oleic acid (OA) ($C_9H_{19}$=$C_9H_{15}COOH$, 99%), phenyl ether ($C_{12}H_{19}O$, 99%), 1,9-nonanedithiol (NDT) ($SHC_9H_{18}SH$, 95%), 11-mercaptoundecanoic acid (MUA) ($SHC_{11}H_{22}CO_2H$, 95%), and other solvents (hexane and ethanol) were purchased from Aldrich. Gold acetate (Au(OOCCH₃)₃, or Au(Ac)₃, 99.9%) was purchased from Alfa. All chemicals were used as received.

The preparation of Fe₃O₄/Au involved an initial synthesis of Fe₃O₄ nanoparticles as seeds and a subsequent reduction of Au(OOCCH₃)₃ in the presence of the seeds. Fe₃O₄ nanoparticles seeds were synthesized using a modified protocol. Briefly, 0.71 g Fe(acac)₃ (2 mmol) was mixed in 20 mL phenyl ether with 2 mL oleic acid (~6 mmol) and 2 mL oleylamine (~6 mmol) under argon atmosphere with vigorous stirring. 2.58 g 1,2-hexadecanediol (10 mmol) was added into the solution. The solution was heated to 210° C. and refluxed for 2 hours. After refluxing for 2 hrs and cooling down to room temperature, the reaction solution was directly used without separation. In a typical synthesis, 10 mL of the phenyl ether reaction solution of Fe₃O₄ nanoparticles (~0.33 mmol Fe₃O₄), 0.83 g (2.2 mmol) Au(OOCCH₃)₃, 3.1 g (12 mmol) 1,2-hexadecanediol, 0.5 mL (~1.5 mmol) oleic acid, 3 mL (~9 mmol) oleylamine were added into 30 mL phenyl ether. In this case, the mole ratio of the Au-precursor to the iron oxide nanoparticles was approximately 7:1. Under argon atmosphere and vigorous stirring, the reaction solution was heated to 180~190° C. at 10° C./min and was kept at this temperature for 1.5 hrs. After cooling down to room temperature, ethanol was added into the solution. A dark purple material was precipitated and separated by centrifuging. The precipitated product was washed with ethanol, and re-dispersed in hexane in the presence of ~75 mM each of oleic acid and oleylamine. The nanoparticle solution appeared dark purple. The product nanoparticles dispersed in hexane can be further separated by centrifugation to obtain the desired core-shell Fe₃O₄/Au nanoparticles. A Hermle Labortechnik GMbH Z 233 M2 centrifuge was used.

Figure 2:
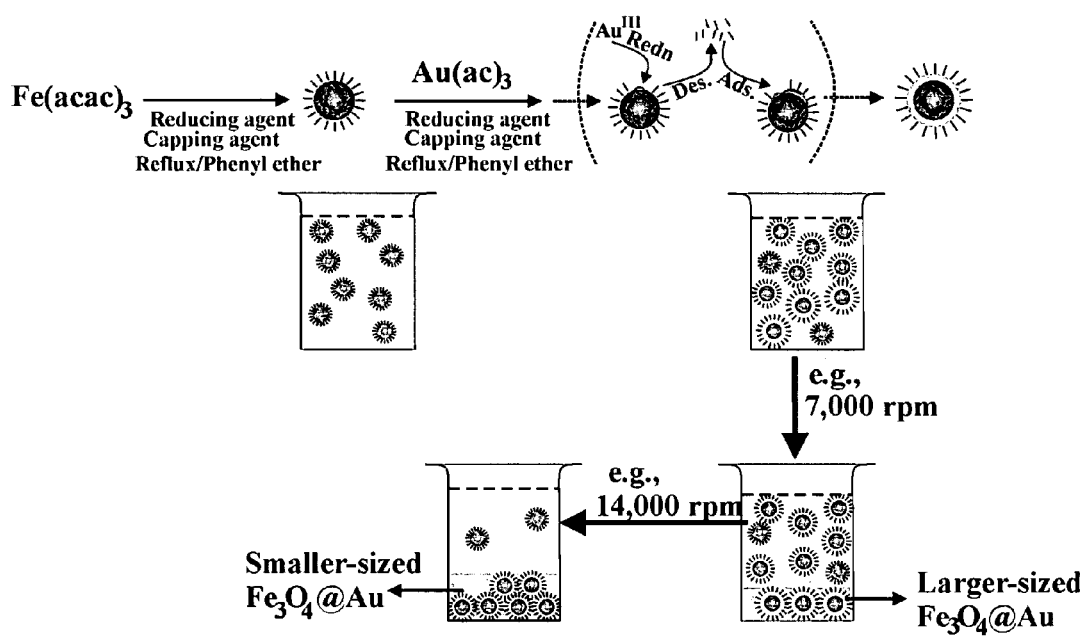
FIG. 2 is an illustration of the chemistry and processes involved in the synthesis of the $Fe_3O_4$ and $Fe_3O_4$/Au nanoparticles by the instant method.

FIG. 2 illustrates the chemistry and processes involved in the synthesis of the Fe₃O₄ and Fe₃O₄/Au nanoparticles. With the desired seeds, two new protocols were used in this work. First, gold was deposited onto Fe₃O₄ via reduction of Au(Ac)₃ in the presence of the seeds and capping agent by a reducing agent at elevated temperature (180-190° C.). This process involves thermally-activated desorption of the capping layer, deposition of Au on the exposed Fe₃O₄ surface, and subsequent re-encapsulation of Au surface by the capping agent.

Second, the resulting Fe$_3$O$_4$/Au nanoparticles were separated by centrifugation, which is very effective in separating Fe$_3$O$_4$ and Fe$_3$O$_4$/Au nanoparticles and different sizes as well. The nanoparticle solution was first centrifuged at 7,000 rpm for 20 minutes, after which some precipitate was observed at the bottom of the tube (coarse fraction) and the top solution still showed a dark purple color. The top dark purple solution was transferred into a new centrifuge tube and re-centrifuged at 14,000 rpm for 20 minutes, after which more dark precipitate was found at the bottom of the tube (fine fraction). The top solution displayed yellow brown color which appears to be a much-diluted solution of Fe$_3$O$_4$. This process can be repeated for many times and the speed can be varied as desired.

The nanoparticles were assembled as a thin film on different substrates including cleaned glass slides and gold film coated glass slides for analysis and characterization. The following techniques were used. Transmission electron microscopy (TEM) was performed on a Hitachi H-7000 Electron Microscope (100 kV). The nanoparticle samples dispersed in hexane solution were cast onto a carbon-coated copper grid sample holder followed by evaporation at room temperature. High resolution transmission electron microscopy (HRTEM) was carried out using JEOL JEM 2010F with an acceleration voltage of 200 kV and a routine point-to-point resolution of 0.194 nm.

Fourier transform infrared spectroscopy (FTIR) was used to characterize the shell structure. The spectra were acquired with a Nicolet 760 ESP FT-IR spectrometer that was purged with boil-off from liquid N$_2$. The spectrometer was equipped with a liquid nitrogen-cooled HgCdTe detector. The nanoparticle powder sample was mixed with KBr powder and ground into fine powders which were pressed into pellets at 15,000 psi. The solution sample was measured using a thin layer (0.5 mm) IR cell. The IR spectra were collected over the range of 400-4000 cm$^{-1}$.

Direct current plasma-atomic emission spectroscopy (DCP-AES) was used to analyze the composition, which was performed using an ARL Fisons SS-7 DCP-AES. Standards and unknowns were analyzed 10 times each for 3 second counts. Thermogravimetry analysis (TGA) was performed with a Perkin-Elmer Pyris-1 thermogravimetric analyzer.

X-ray powder diffraction (XRD) was used to characterize the crystallinity of the products. Powder diffraction patterns were recorded on a Scintag XDS 2000 θ-θ powder diffractometer equipped with a Ge(Li) solid-state detector (CuKα radiation).

X-ray photoelectron spectroscopy (XPS) measurements were made using a Physical Electronics Quantum 2000 scanning ESCA microprobe. The percentages of individual elements detected were determined from the relative composition analysis of the peak areas of the bands. The relative peak areas and their corresponding sensitivity factors were used to compute the relative compositions.

Superconducting Quantum Interference Device (SQUID) magnetometric measurements were performed using a SQUID magnetometer (Quantum Design MPMS XL-5). The temperature dependence of the magnetic susceptibility ($\chi$=M/H, where M is the magnetization and H is the applied magnetic field) was measured as a function of temperature in a magnetic field.

Figure 3A:
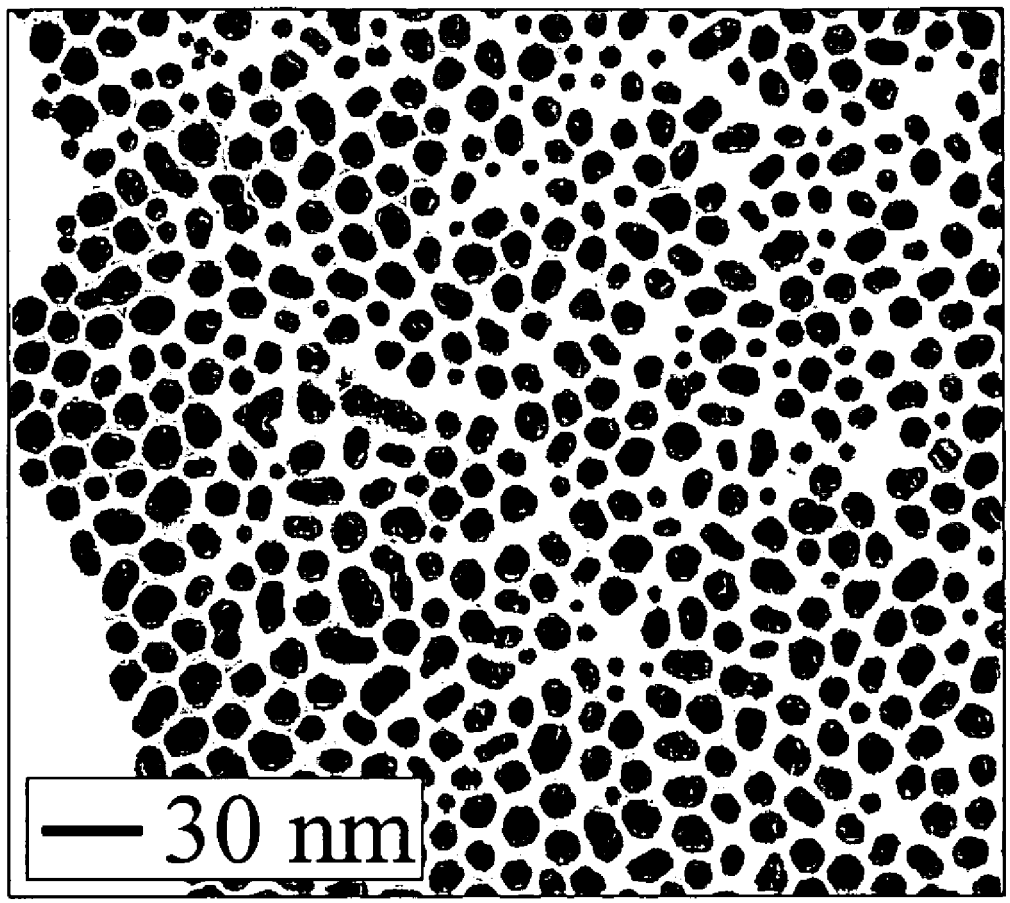
FIGS. 3a-3c show TEM micrographs for $Fe_3O_4$/Au collected from the precipitate after centrifugation.
Figure 3B:
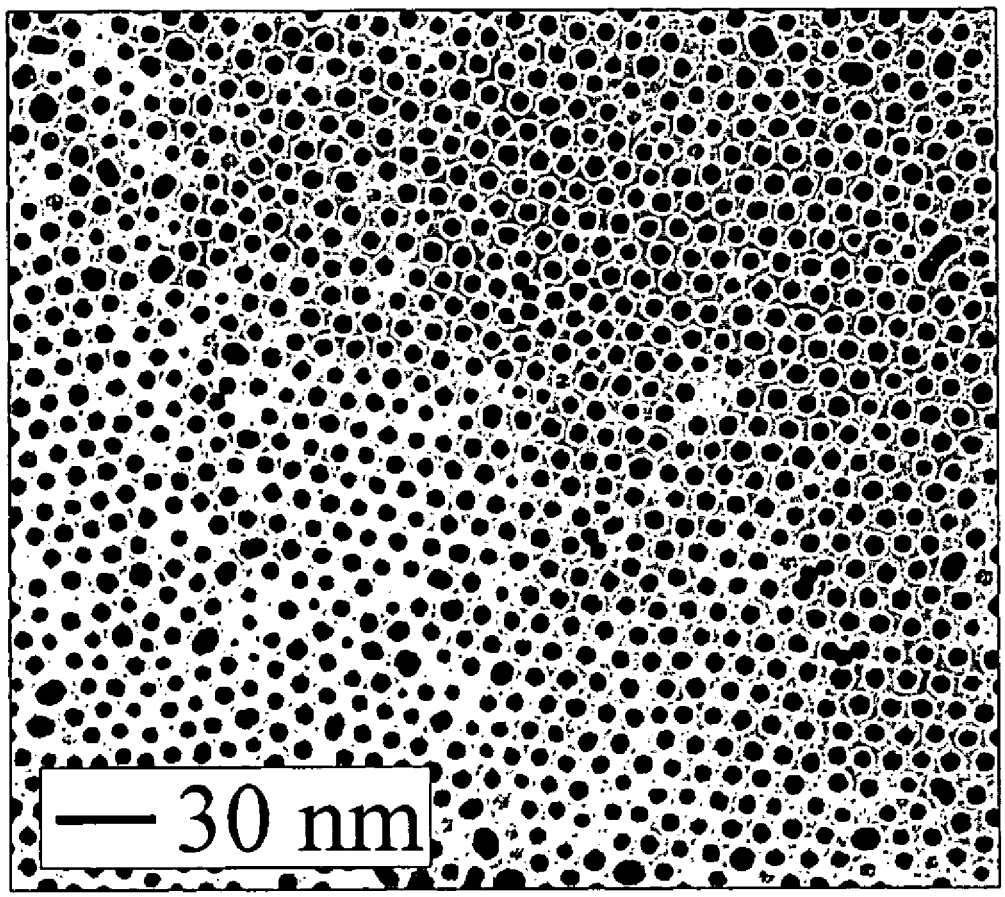
Figure 3C:
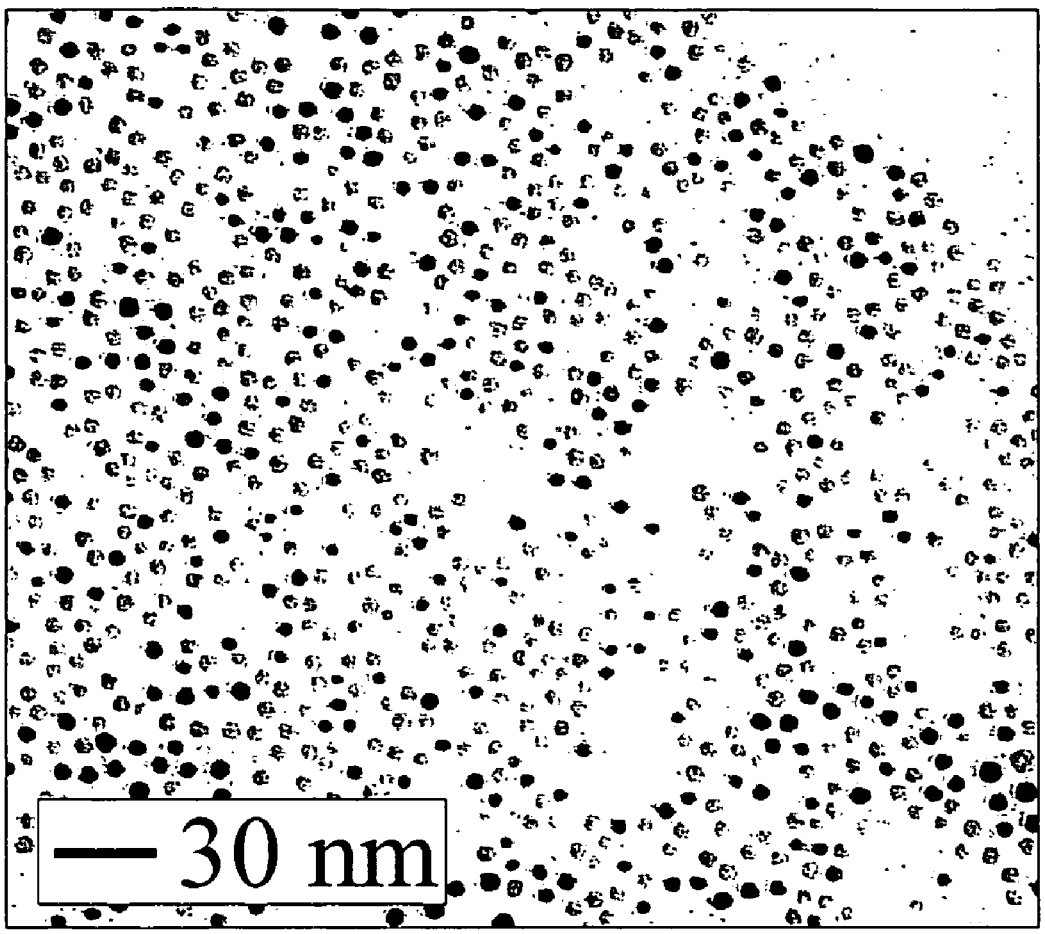

FIGS. 3a-3c show a representative set of TEM images for the Fe$_3$O$_4$/Au nanoparticles collected from the above separation processes, including those collected from the precipitate after centrifugation at 7000 rpm (FIG. 3a), the precipitate by re-centrifuging the top solution at 14000 rpm (FIG. 3b), and the final top solution portion after both the 7000- and 14000- rpm centrifugations (FIG. 3c). There are clear differences in sizes. The particles collected after the first 7000 rpm centrifugation had larger average core size (12.1±1.4 nm), whereas the particles collected from the precipitate by re-centrifuging the top solution at 14000 rpm had a smaller average core size (6.6±0.4 nm). Based on the change of the absorbance for the surface plasmon resonance band, a rough estimate of the ratio of A:B in terms of quantities, yielded 12:88. In contrast, the particles collected from the top solution portion (FIG. 3c) were predominantly uncoated Fe$_3$O$_4$ nanoparticles (5.3±0.5 nm), which is supported by the darkness contrast of the particles.

Table 1 shows the atomic weight ratios of Au and Fe, confirming complete coverage of the seed particles; the thickness of the shell is also given.

TABLE 1

Results from DCP analysis of metal compositions in the nanoparticles (core size: 5.2 nm)

| Sample | Atomic weight ratio (AR) Au:Fe | Shell thickness d (nm) |
| --- | --- | --- |
| As-synthesized Fe$_3$O$_4$/Au powder | 44:56 | 0.4 |
| Separated Fe$_3$O$_4$/Au at 7k rpm | 71:29 | 1.0 |
| Separated Fe$_3$O$_4$/Au at 14k rpm | 66:34 | 0.8 |

Figure 4A:
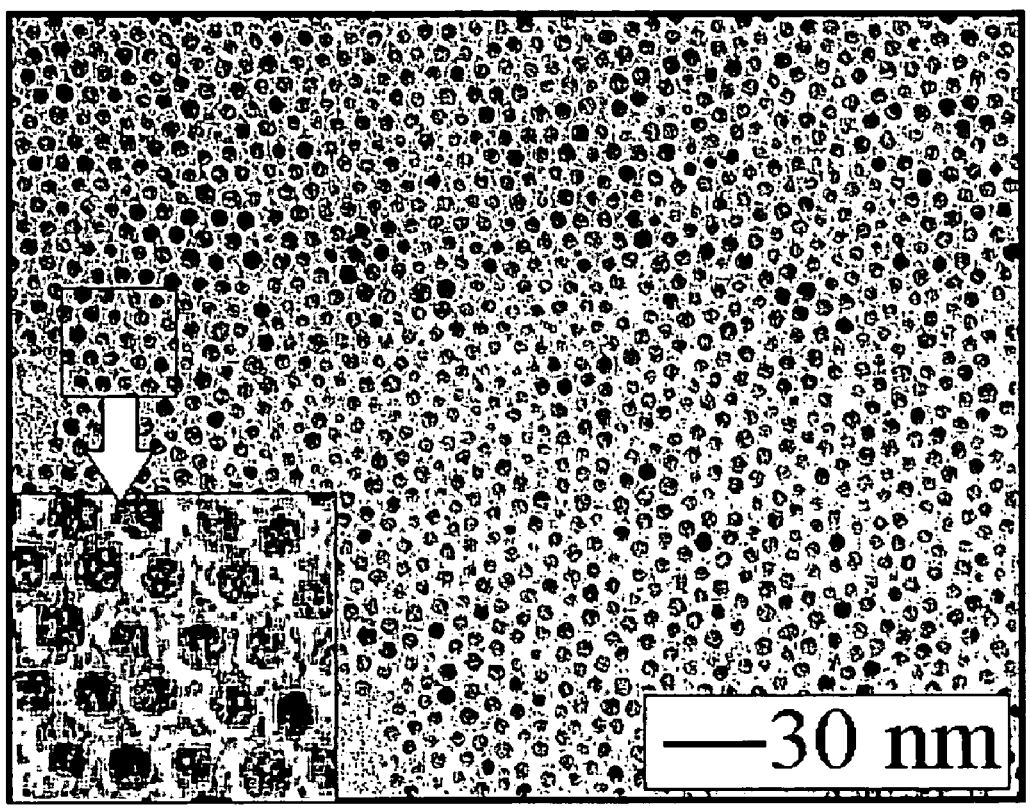
FIGS. 4a-4d are TEM micrographs and size distributions for $Fe_3O_4$ nanoparticles before and after coating with Au shell.
Figure 4B:
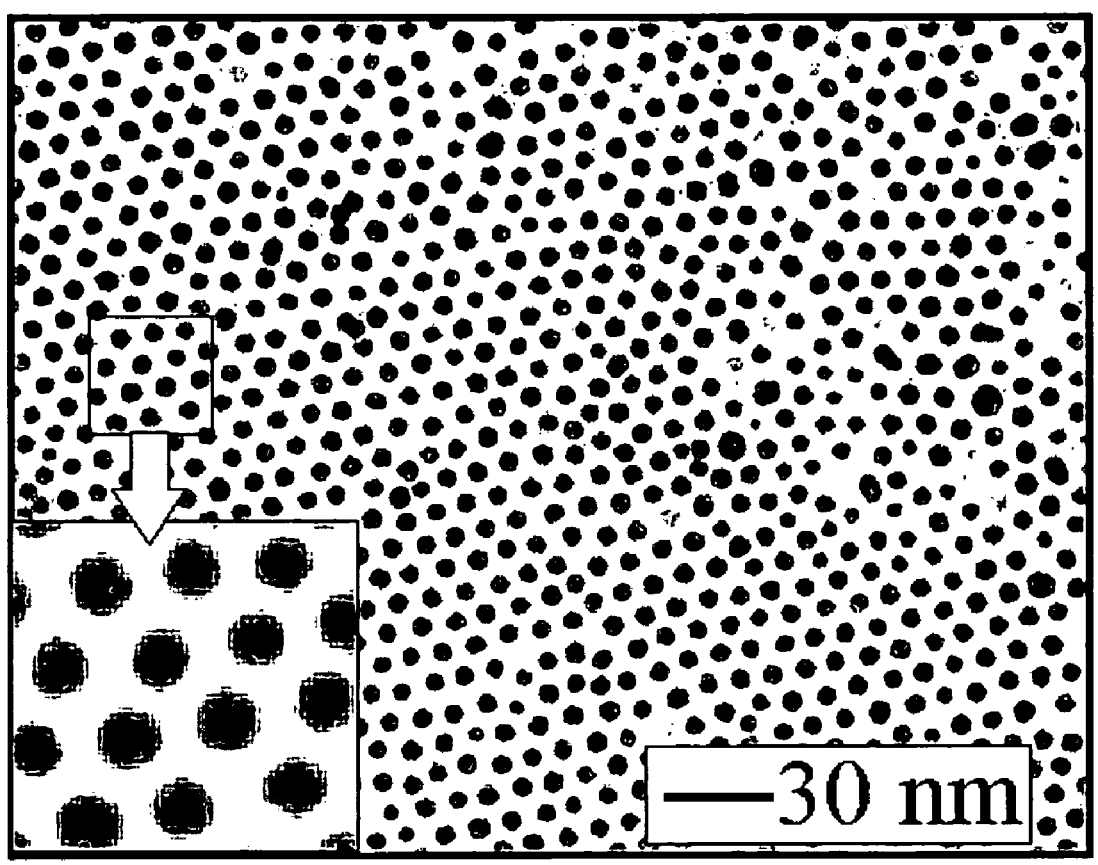
Figure 4C:
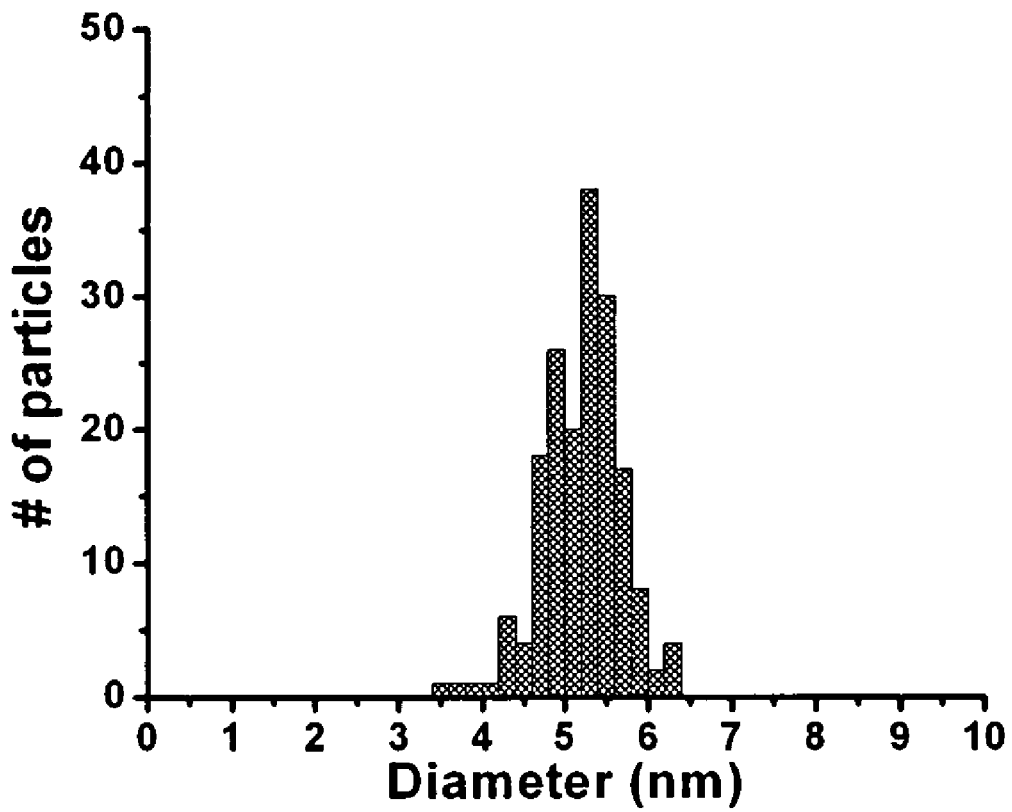
Figure 4D:
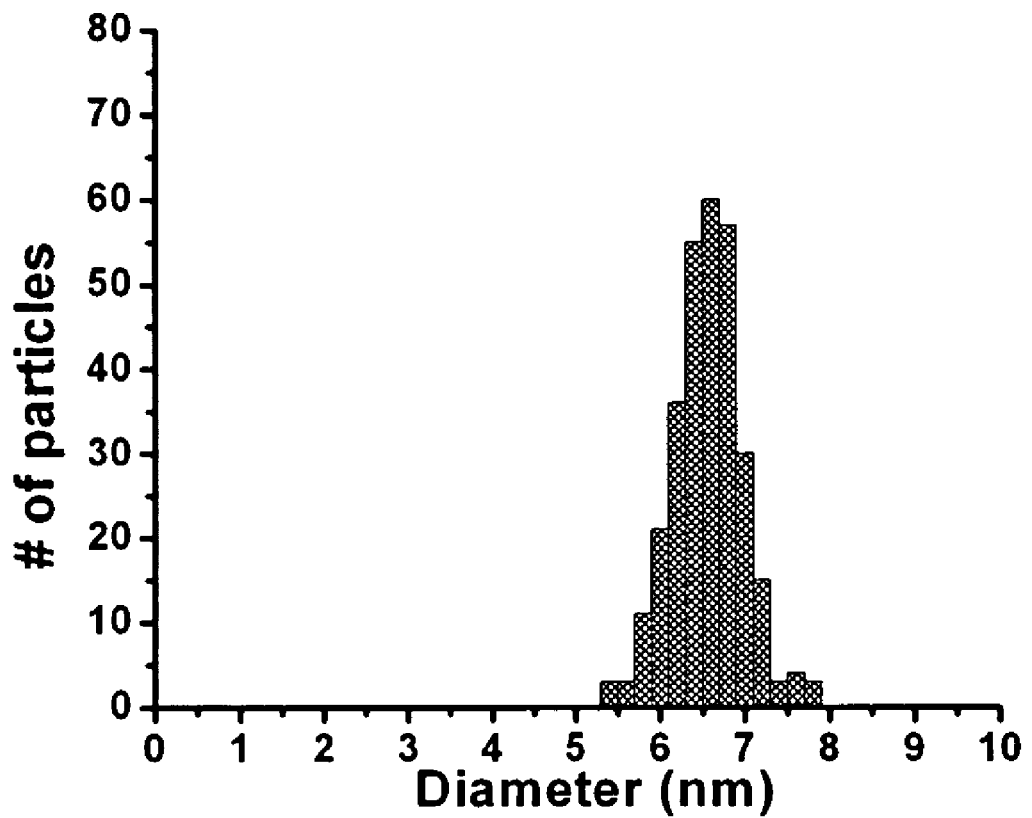
Figure 16A:
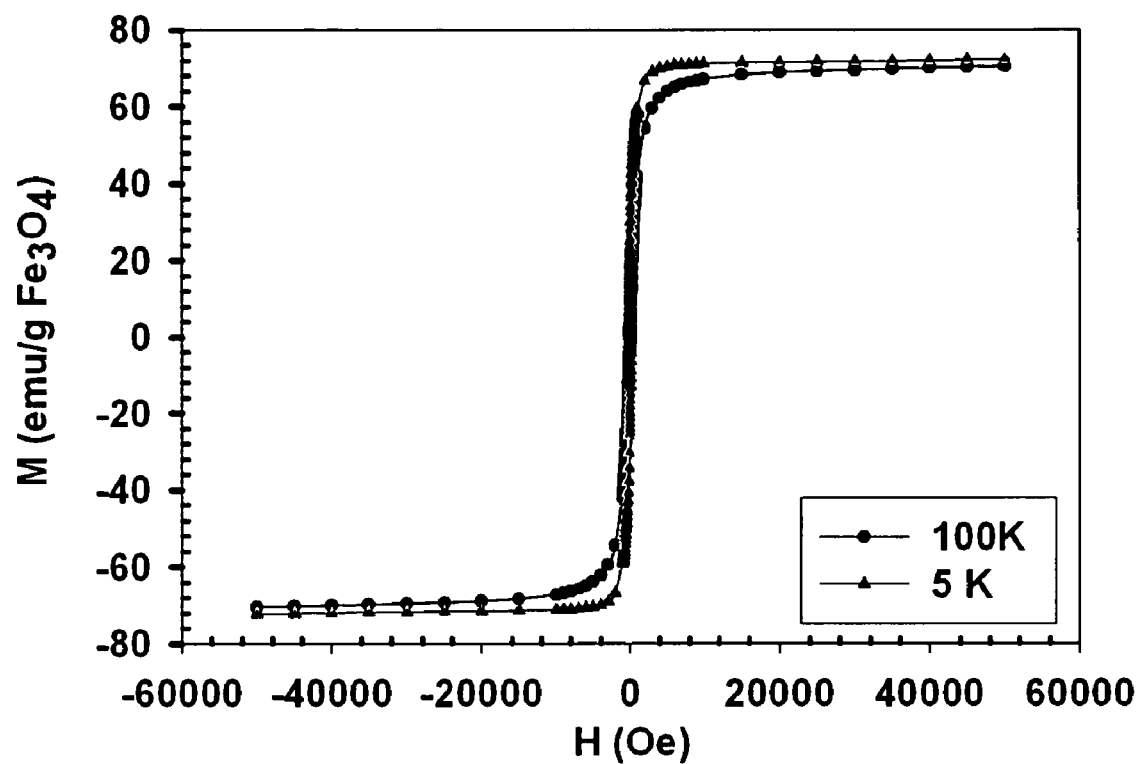
FIGS. 16a-16d show the magnetization and coercivity of oxide core and metal-coated core/shell particles.
Figure 16B:
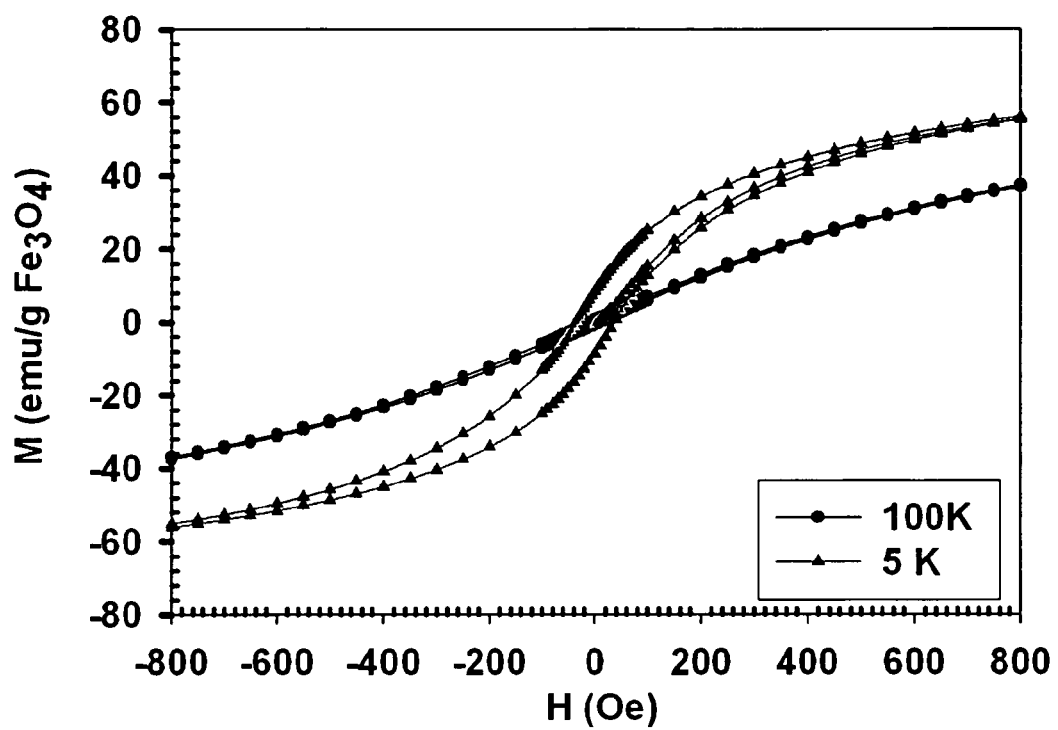
Figure 16C:
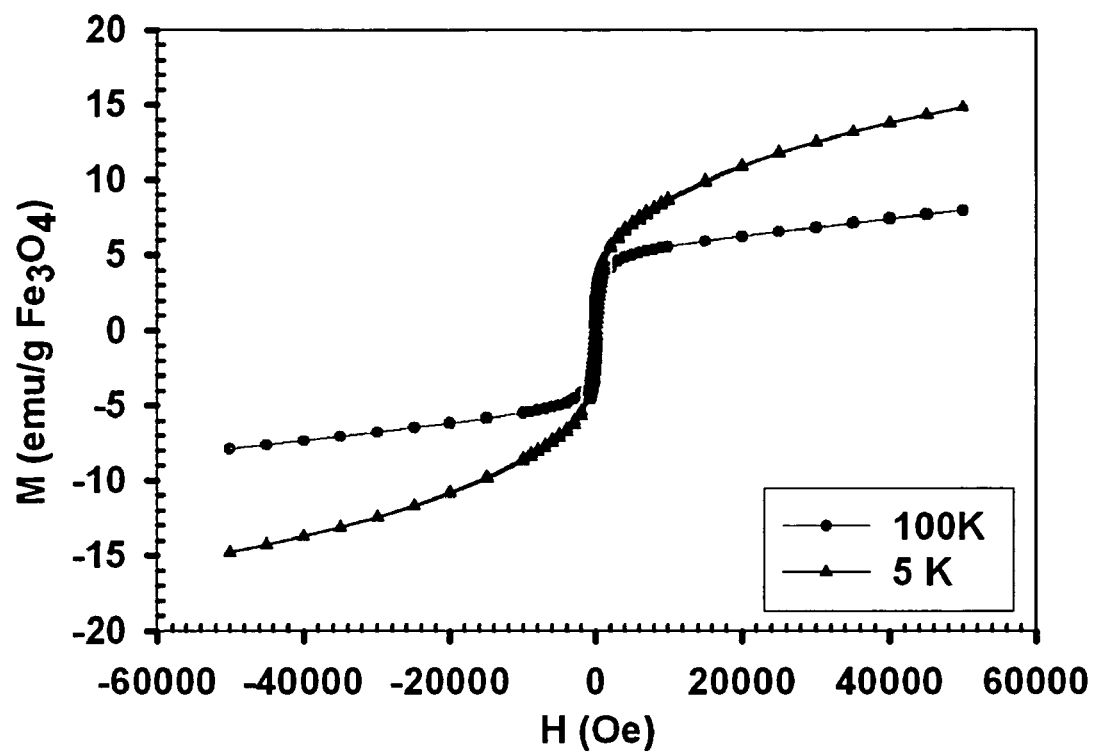
Figure 16D:
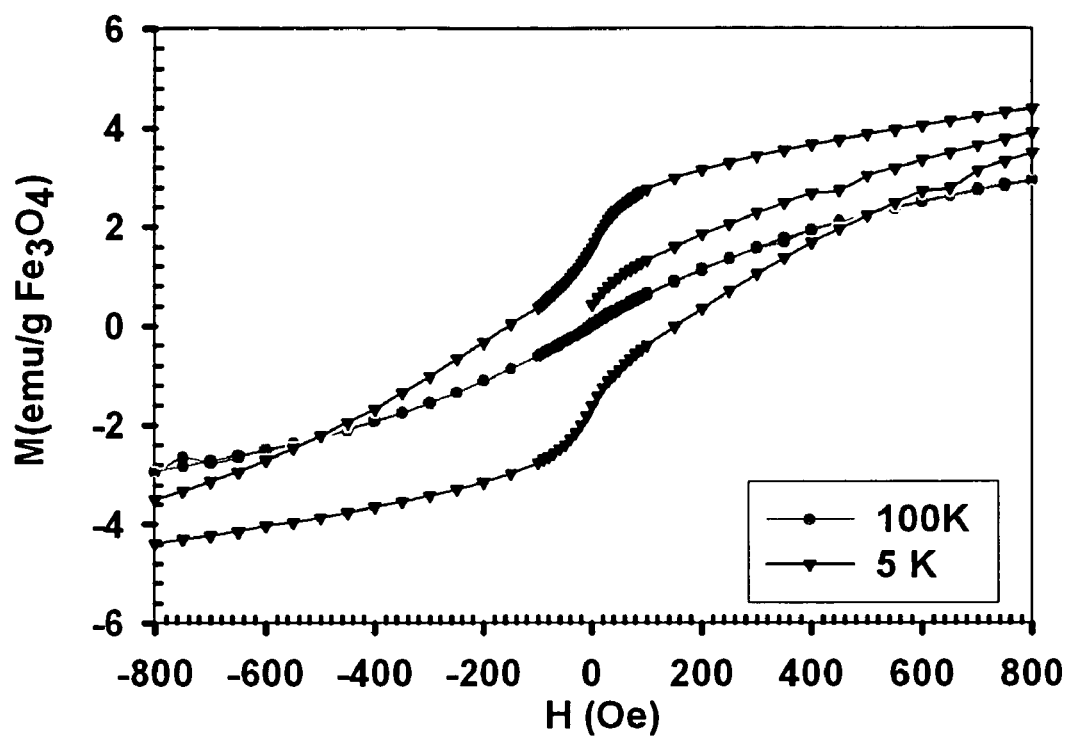

FIGS. 4a-4d show the images and size distribution of the Fe$_3$O$_4$ core seeds and the coated nanoparticles obtained from the above process. The uncoated core seeds are shown in FIG. 4a and the corresponding particle size distribution in FIG. 4c. The fine fraction nanoparticles obtained after centrifugation is shown in FIG. 4b and the particle size distribution in FIG. 4d. The magnetic properties of the uncoated oxide particles (FIG. 16a, 16b) and the core/shell particles (FIG. 16c, 16d) are compared. The magnetization curves (FIGS. 16a, 16c) and the coercivity (FIGS. 16b, 16d) of the particles confirm their superparamagnetic characteristics.

Example 2

Figure 5A:
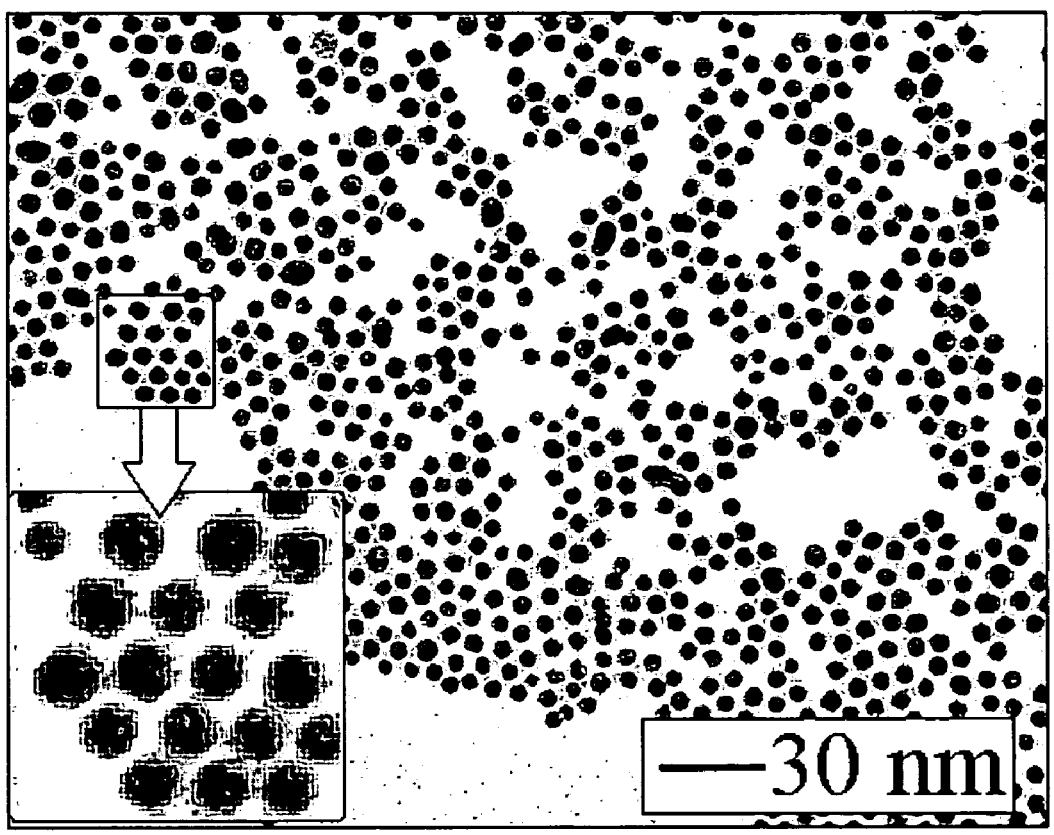
FIGS. 5a and 5b show TEM micrograph and size distribution for $Fe_3O_4$/Au nanoparticles derived from another core size.
Figure 5B:
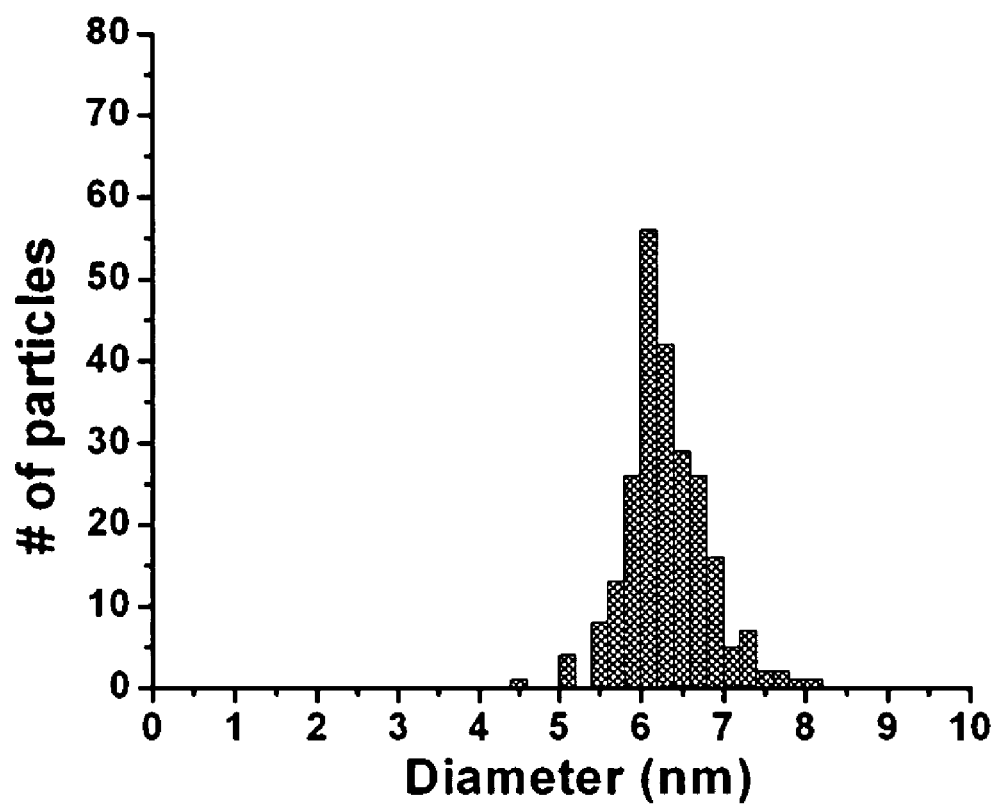

The method of Example 1 was repeated except that the reflux time in the preparation of the Fe$_3$O$_4$ core seed was reduced from 2 hours to 1.5 hours. The average core seed diameter decreased from 5.2 nm to 4.5 nm. The size of the coated Fe$_3$O$_4$/Au nanoparticles obtained after the final centrifugation also decreased. These are shown in FIGS. 5a and 5b. The average coating thickness increased from 0.7 nm of example 1 to 0.9 nm.

Figure 7:
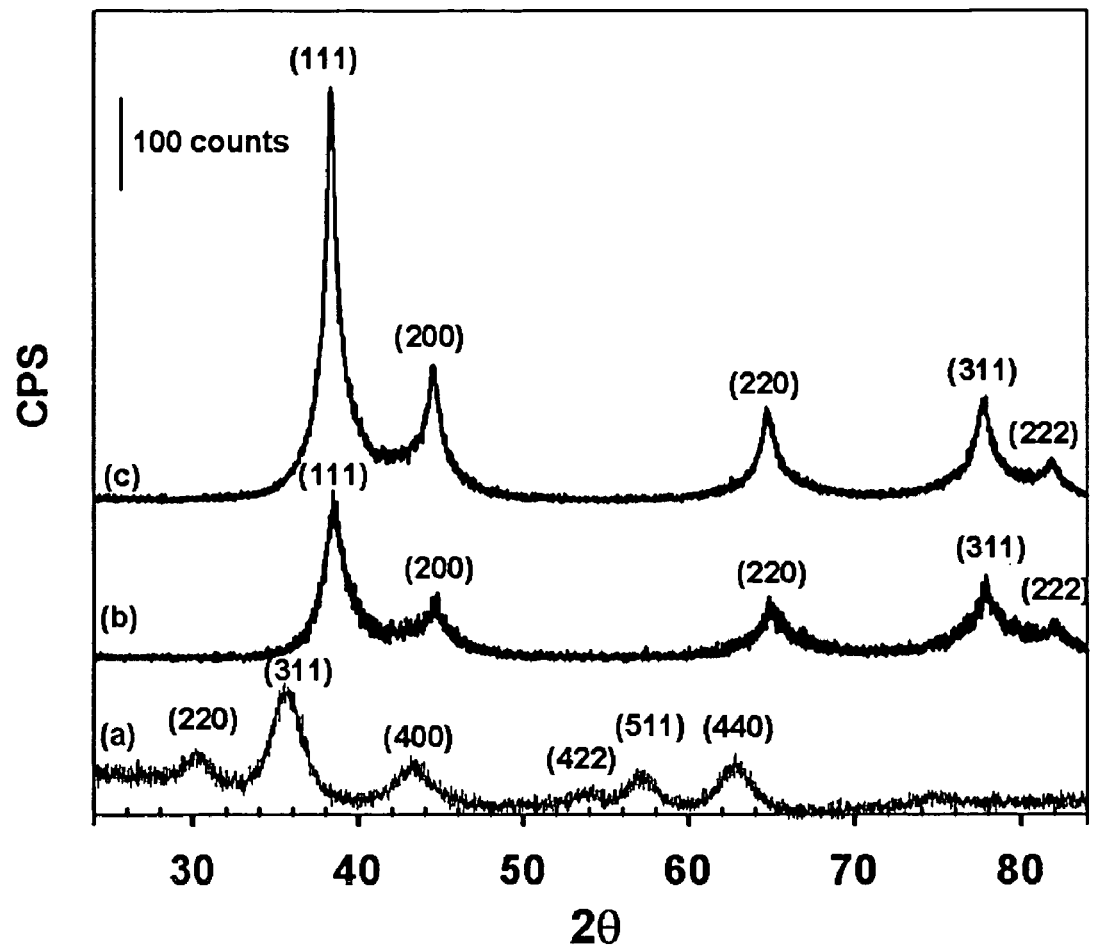
FIG. 7 is an X-ray diffractogram of the samples.

XRD spectra from the uncoated and coated samples are shown in FIG. 7. The diffraction patterns of (a) Fe$_3$O$_4$ before coating (b) pure Au and (c) Fe$_3$O$_4$/Au coated nanoparticles are compared. The absence of Fe$_3$O$_4$ peaks in the coated sample further confirms that the Au-shell completely covers the core.

Figure 6:
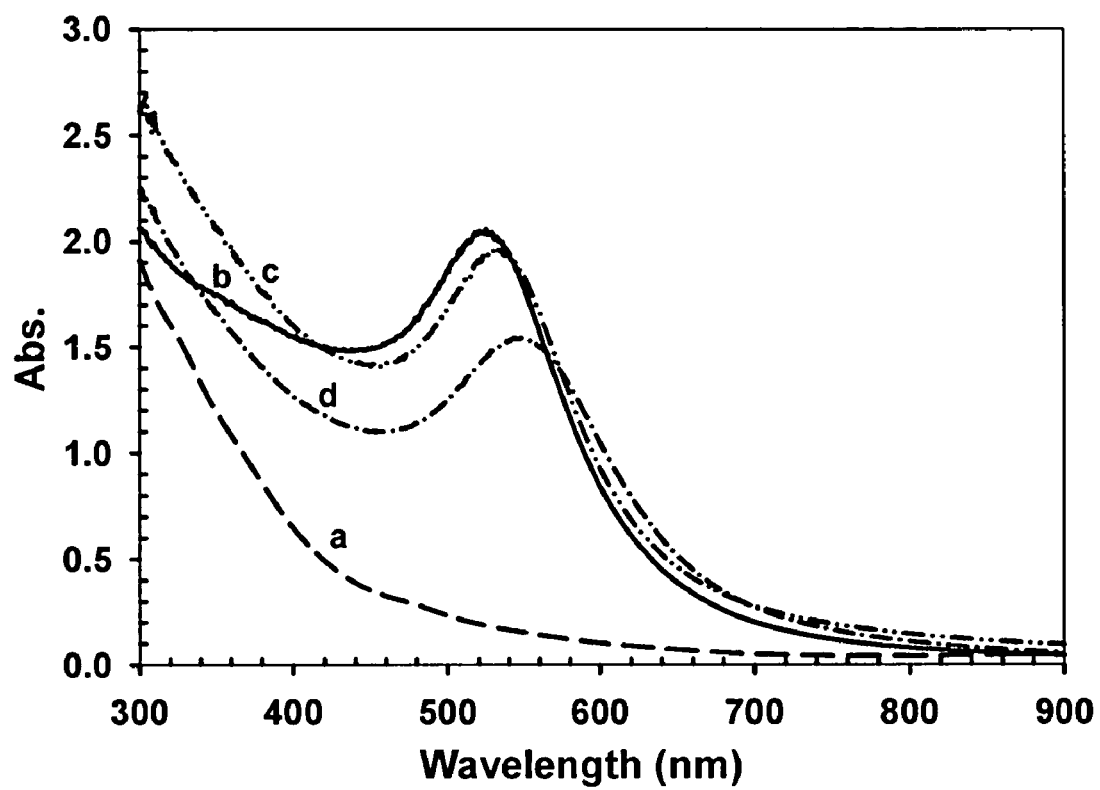
FIG. 6 is a plot of UV and visible spectra of the samples of FIGS. 4a and 5a, respectively.

FIG. 6 shows a typical set of UV-Vis spectra comparing Fe$_3$O$_4$ (a) and Fe$_3$O$_4$/Au (c, d) nanoparticles dispersed in hexane solution. In contrast to the largely silent feature in the visible region for Fe$_3$O$_4$ particles, Fe$_3$O$_4$/Au particles show a clear SP band at 535 and 550 nm for the different core sizes and Au thickness, characteristic of the optical property of gold nanostructure. This band showed a red shift in comparison with pure Au nanoparticles capped with oleylamine (b) that were synthesized by the same method. It may be seen that the core-shell nanoparticles with a thicker Au shell (c) displayed a smaller red shift than those with thinner Au shells (d). This finding suggests that the surface plasmon resonance property is affected by the distance to the oxide core. As will be further supported by DCP analysis data described hereinbelow, the probability of a significant number of pure gold nanoparticles in these core-shell nanoparticle samples is low.

Example 3

In a process similar to that in Example 1, $\gamma$-$Fe_2O_3$ core seeds were formed by oxidation of $Fe(CO)_5$. With $\gamma$-$Fe_2O_3$ cores, a hexane solution of the core nanoparticles was mixed with phenyl ether and a solution of $Au(OOCCH_3)_3$ with oleic acid, oleylamine and 1,2-hexadecanediol. After reaction under heating, the mixture was cooled down to room temperature. The rest of the preparation steps were the same as the synthesis of $Fe_3O_4$/Au. The thickness was controlled by adjusting the ratio between the gold precursor and the core seeds. The average yield to the formation of gold shell was about 90%.

Example 4

Water-dispersible iron oxide/Au nanoparticles were also prepared. In one method, the hydrophobic iron oxide/Au nanoparticles were made water-dispersible by ligand exchange or mixing nanoparticles with bipolar molecules. The ligands used were bifunctional molecules such as $HS(CH_2)_nCOOH$, $H_2N(CH_2)_nNH_2$, or $H_2N(CH_2)_nCOOH$. For example, the hexane dispersion of $Fe_3O_4$/Au nanoparticles was mixed with a saturated solution of mercaptoundecanoic acid in cyclohexyl ketone. After shaking for 10 minutes, the oleic acid/oleyl amine ligands on $Fe_3O_4$/Au shell can be replaced by mercaptoundecanoic acid to give water-dispersible nanoparticles (in pH=10~14). To a hexane dispersion of $Fe_3O_4$/Au nanoparticles was added a suspension of teramethylammonium 11-aminoundecanoate in dichlormethane. The resulting mixture was shaken for 30 minutes; the precipitate of nanoparticles was washed with dichloromethane, and then dried to produce precipitates under $N_2$. The final product was dispersed in water.

In another method, water-soluble iron oxide (FeOOH) nanoparticles were first produced by thermal treatment of iron-storage protein ferritin. This treatment involved heating ferritin proteins deposited on a planar silicone substrate under 500° C. in air which removed the protein shell. The nanoparticles were dispersed in aqueous solution by controlled sonication of the wafer in deionised water at a controlled temperature. Iron oxide nanoparticles having diameters in the range of 5-20 nm were produced. Further reaction of the FeOOH cores in the presence of water-soluble Au-precursors (e.g. $HAuCl_4$) and reducing agent (e.g., citrate) produced FeOOH core/Au shell nanoparticles. The thickness of the gold shell depends on the choice of the Au-precursor and the reducing agent, their concentrations, and the reaction temperature.

According to the thin film assembly procedures NDT or MUA molecules were mixed with nanoparticles in a hexane solution, 10 mM NDT+0.2 µM $Fe_3O_4$/Au nanoparticles for the NDT-assembly, and 0.06 mM MUA+0.1 µM $Fe_3O_4$/Au for the MUA-assembly. The concentration of $Fe_3O_4$/Au nanoparticles was estimated using several parameters including the initial feeding of Fe, the density of iron oxide, the average diameter of the particle, and the yield of the resulting core-shell nanoparticles. The nanoparticles were assembled as a thin film on different substrates including cleaned glass slides and gold film coated glass slides. The glass slides were used for spectrophotometric measurement. The substrates were immersed vertically in the solution to ensure the film was free of powder deposition. The thin film was thoroughly rinsed with hexane and dried under nitrogen or air before characterizations.

The thickness (or coverage) was controlled by assembling time and monitored by surface plasmon (SP) resonance absorbance and mass loading.

The thin film formation was examined by monitoring optical properties. The color of the film formed ranged from brown to blue depending on the particle size, linker molecule and film thickness. This is similar to thin film assemblies of gold nanoparticles. Table 2 summarizes the several sets of the experimental results.

TABLE 2

The formation of thin films on glass substrate for different nanoparticles and linkers.

| Nanoparticle | Linker | Film Assembly | λ (SP band) (nm) |
|---|---|---|---|
| $Fe_3O_4$ | NDT | No | — |
|  | MUA | No | — |
| $Fe_3O_4$/Au | NDT | Yes | 610 |
| ($Fe_3O_4$ core size: | MUA | Yes | 600 |
| 5.2 nm) | NDT | Yes | 600 |
| $Fe_3O_4$/Au | MUA | Yes | 590 |
| ($Fe_3O_4$ core size: | NDT | Yes | 590 |
| 4.5 nm) | MUA | Yes | 580 |
| Au |  |  |  |

In comparison with the SP band for $Fe_3O_4$/Au nanoparticles in solution, the SP band is shifted to a longer wavelength for NDT- or MUA-mediated thin film assemblies of $Fe_3O_4$/Au nanoparticles. This trend is similar to that observed for the NDT- or MUA-mediated thin film assemblies of Au nanoparticles of similar sizes. The shift of the SP band is characteristic of the changes in interparticle spacing and dielectric properties as a result of the thin film assembly. In contrast, thin films were not detected for the assembly of $Fe_3O_4$ nanoparticles under the same conditions. The results are consistent with the Au-thiolate binding chemistry responsible for the formation of $Fe_3O_4$/Au thin films. It was noted that the nanoparticle solution became clear after approximately 10 days for the case of NDT-mediated assembly, suggesting an assembly efficiency of ~100%. In the case of MUA-mediated assembly, the solution showed a color change from dark red to light red after 5 days, suggesting assembly efficiency of <100% during the time frame of the experiment.

It is important to note that the assembly scheme via the thiol-thiol exchange is successful only for the Fe oxide/Au core-shell nanoparticles due to the Au-SR binding affinity. In contrast, the self-assembly scheme is not successful for iron oxide nanoparticles because of the lack of binding affinity.

Figure 8:
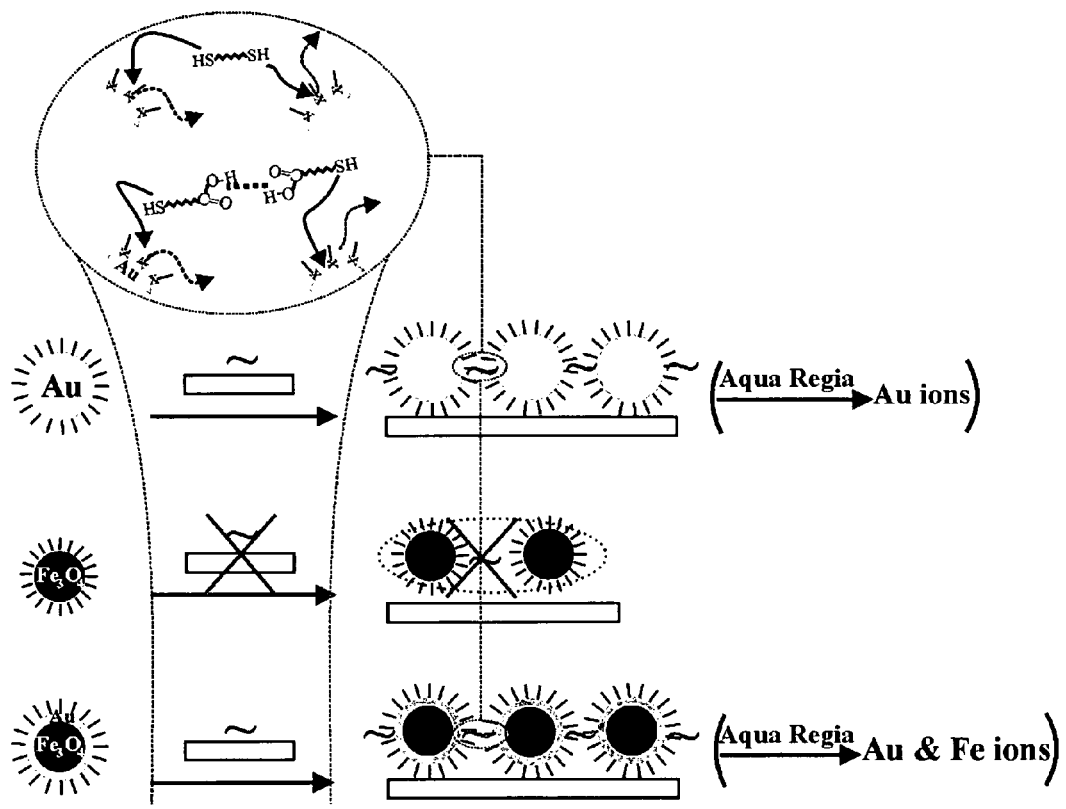
FIG. 8 illustrates a thiol-mediated thin film assembly of Au, $Fe_3O_4$ and $Fe_3O_4$/Au nanoparticles on a substrate.

The chemistry of the exchange process is illustrated in FIG. 8. Conventional thiol-mediated thin film assembly of Au nanoparticles is shown on the top, $Fe_3O_4$ core seeds in the middle and $Fe_3O_4$/Au nano particles at the bottom of the figure. The insert also illustrates the two types of bifunctional thiol-mediated interparticle binding chemistry. In FIG. 8, S represents the functional groups (oleic acid, oleylamine or dodecane thiol).

The composition of the assembled films was analyzed using several methods. One assaying method included dissolution of the film in aqua regia as shown in FIG. 8. The solution was then analyzed using a DCP-AES technique.

The measured metal shell thickness of the capped core/shell nanoparticles shows uniformity and consistency as shown in Table 3.

TABLE 3

Results from DCP analysis of metal compositions in the nanoparticle thin films

| Sample | Atomic weight ratio (AR) Au:Fe | Shell thickness d (nm) Base on DCP | Base on TEM |
|---|---|---|---|
| ($Fe_3O_4$ core size: 5.2 nm) | | | |
| $Fe_3O_4$/Au NPs | 44:56 | 0.4 | 0.7 |
| NDT- $Fe_3O_4$/Au film | 53:47 | 0.6 | 0.7 |
| MUA- $Fe_3O_4$/Au film | 64:36 | 0.8 | 0.7 |
| ($Fe_3O_4$ core size: 4.5 nm) | | | |
| $Fe_3O_4$/Au NPs | 71:29 | 0.9 | 0.9 |
| NDT- $Fe_3O_4$/Au film | 71:29 | 0.9 | 0.9 |
| MUA- $Fe_3O_4$/Au film | 63:37 | 0.7 | 0.9 |

A further comparison of the shell thickness estimated from DCP-determined Au:Fe ratios and with the TEM-determined average shell thickness provided useful information. The comparison is based on a spherical core-shell model and the metallic composition (atomic ratio of Au:Fe (AR)), i.e., $3N_{Fe3O4} \times AR = N_{Au}$, where $N_{Fe3O4}$ and $N_{Au}$ represent the number of $Fe_3O_4$ molecules and Au atoms, respectively. The thickness of the Au shell is:

$$d = \frac{D}{2} \times (\sqrt[3]{0.6858 \times AR + 1} - 1) \quad (1)$$

where D is the diameter of $Fe_3O_4$ nanocrystal seeds, and d the thickness of the Au shell. The densities for $Fe_3O_4$ and Au are $\rho(Fe_3O_4)=5.196$ g/cm$^3$ and $\rho(Au)=19.3$ g/cm$^3$. It is remarkable that the shell thickness derived from the DCP-determined Au:Fe ratios according to Eq. 1 is quite comparable to those directly obtained from the TEM-determined average shell thickness.

The average thickness of the Au shell determined from the above data is 0.6 nm and 0.8 nm for particles derived from nanocrystal core sizes of 5.2 nm and 4.5 nm, respectively. The remarkable closeness between the average particle sizes estimated from the DCP analysis of the core-shell nanoparticle composition and those determined from TEM demonstrates that the inventive synthetic approach is very effective for the preparation of the core-shell $Fe_3O_4$/Au nanoparticles and the thin film assemblies. By controlling the reaction time and concentration of the Au precursor, the thickness can be effectively controlled in a wide range.

Figure 9:
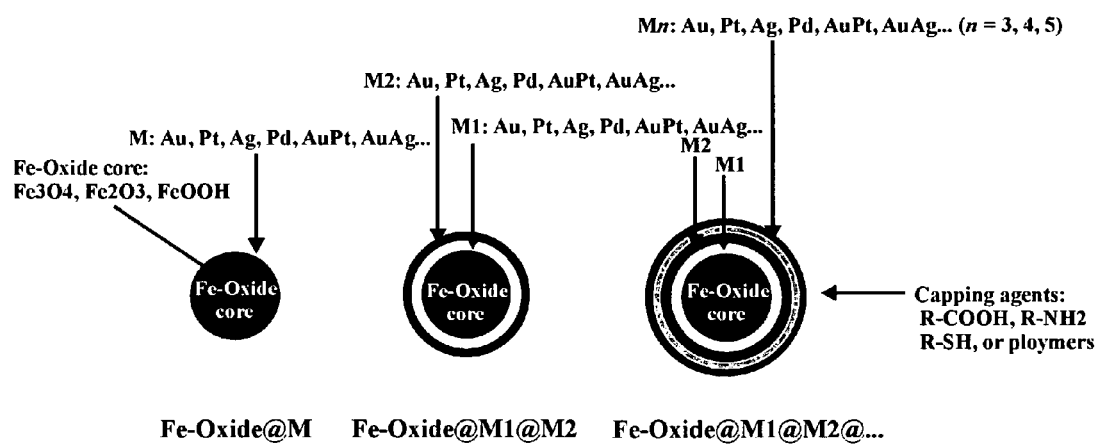
FIG. 9 shows schematic multi-shell composites.

A key element of the synthesis of the core/shell nanoparticles involves sequential formation of Fe-Oxide core, first metal shell (M1) and second metal shell (M2), as illustrated in FIG. 9, via manipulation of the reaction conditions (e.g., temperature and solvent). The presence of the organic capping agents in each step is important for controlling the size and monodispersity of the nanoparticles. Few reports have shown such a general strategy directed at synthesizing these core-shell nanostructures with controlled core-shell composition via sequential core formation followed by shell coating for the electrocatalytic applications.

While a number of core-shell metal nanoparticles are prepared by other or similar approaches such as Pt/Cu, Au/Pt, Au/Pd, Au/Ag, Pt/Co, Ag/Co, Au/Pd, Pt/Ru, Pt/$Fe_2O_3$, FePt/$Fe_3O_4$, Au/silica, polystyrene core/polyelectrolyte shell, etc., few, if any, prior reports have demonstrated the sequential core-shell formation approach to core/shell nanoparticles as targeted in this work (e.g., $Fe_3O_4$/Au/Pt, and $Fe_3O_4$/Pt/Au). One unique aspect of the sequential formation of core and shell is to eliminate the complication of one-step synthesis in which it is often difficult to avoid or suppress unpredictable alloying or phase-segregation. One of the practical advantages in exploring core-shell catalysts is the viability of using stable and less-expensive metals as cores and the active or inexpensive metals as shells in view of the increasing concerns over stability and cost.

Figure 10A:
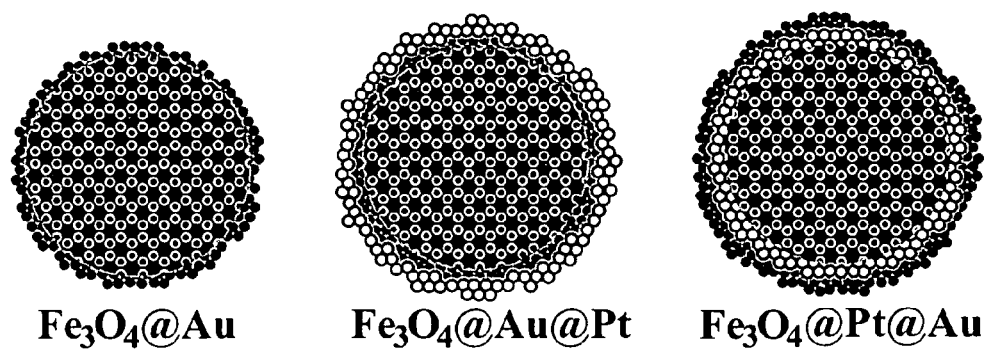
FIG. 10a illustrates and Fe₃O₄/Au, Fe₃O₄/Au/Pt and Fe₃O₄/Pt/Au multi-shell composites.

Fe-oxide based core-shell nanoparticles, such as Fe-Oxide/Au/Pt, /AuPt, and /Au/Pt or /Pt/Au, were synthesized by modifying a novel seeded growth route (see FIG. 9, and FIG. 10a) for the synthesis of $Fe_3O_4$/Au nanoparticles. This route is coupled with thermally activated deposition, core coalescence and re-encapsulation which have been demonstrated above to produce highly monodispersed $Fe_3O_4$/Au with interesting magnetic properties.

Figure 10B:
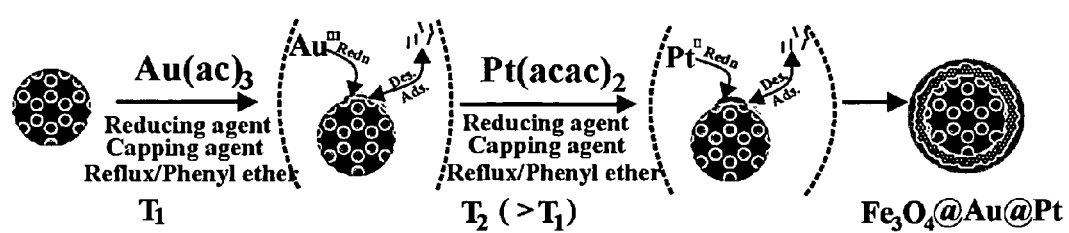
FIG. 10b is a schematic illustration of the sequential formation of $Fe_3O_4$ cores as a function of temperature.
Figure 11:
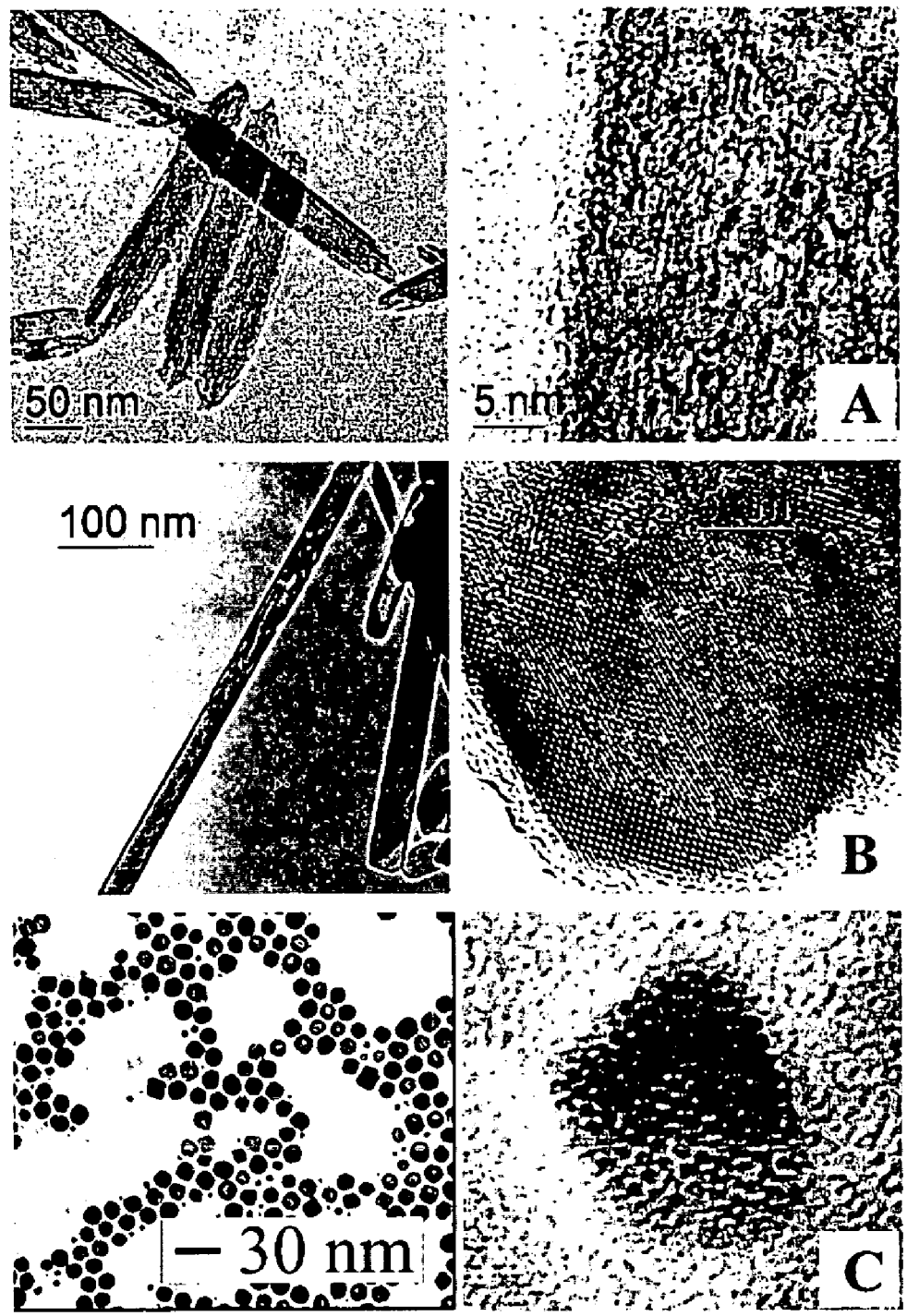
FIG. 11 shows alternative core morphologies such as rods and needles.

The synthesis of Fe-Oxide/Au/Pt is shown: in FIG. 10b which is a schematic illustration of the sequential formation of two metal shells on $Fe_3O_4$ cores.

Figure 12A:
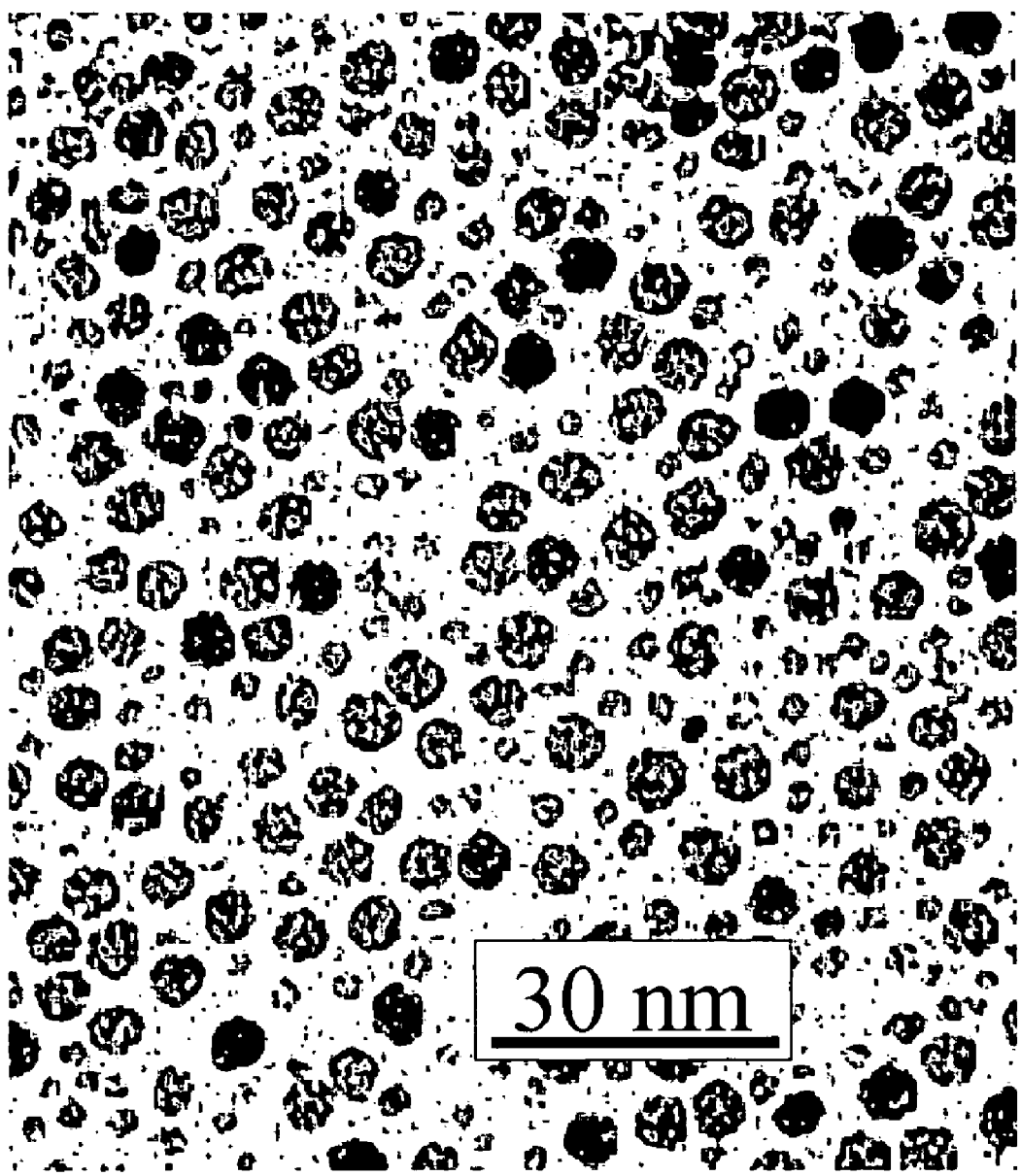
FIGS. 12a-12b depicts TEM contrast images of the uncoated oxide particles and multiple-shell coated oxide particles.
Figure 12B:
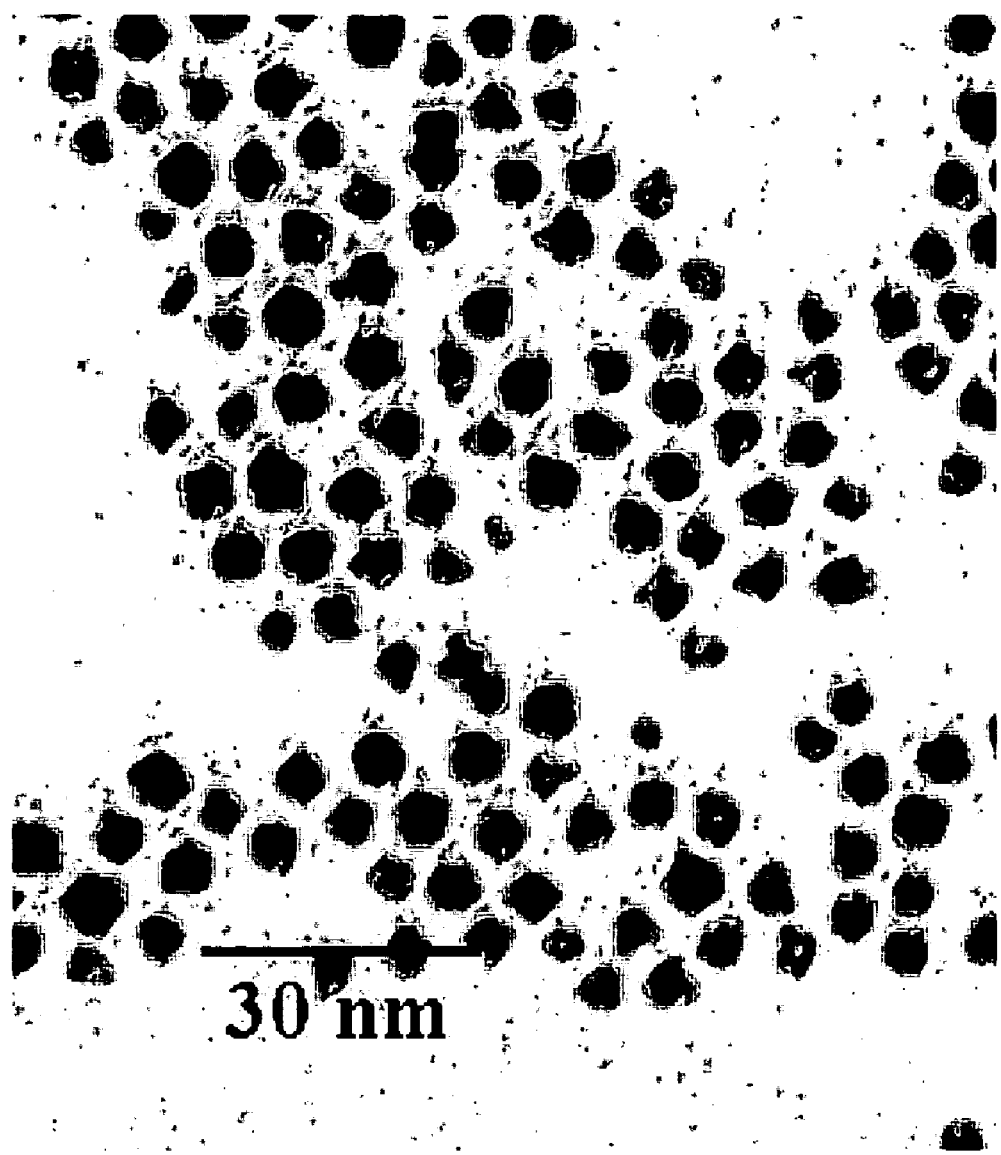

The TEM images in FIGS. 12a and 12b show $Fe_3O_4$ and $Fe_3O_4$/Au/Pt nanoparticles, respectively. The synthesis began with a mixture of Pt(acac)$_2$, Au(ac)$_3$, 1,2-hexadecanediol, oleic acid, OAM and $Fe_3O_4$ nanoparticle seeds in phenyl ether which was slowly heated. In the synthesis, oleic acid and oleylamine were added in phenyl ether solution containing Pt(acac)$_2$, Au(ac)$_3$, 1,2-hexadecanediol, and $Fe_3O_4$ nanoparticle seeds at 80° C. under Ar. The mixture solution was slowly heated to 140-180° C. during which purple color was observed around 140° C. After reaching 180° C., the solution changed to brown, which is due to the formation of $Fe_3O_4$/Au/Pt nanoparticles. This assessment is supported by the sharp contrast and the subtle size difference in TEM images.

Figure 13:
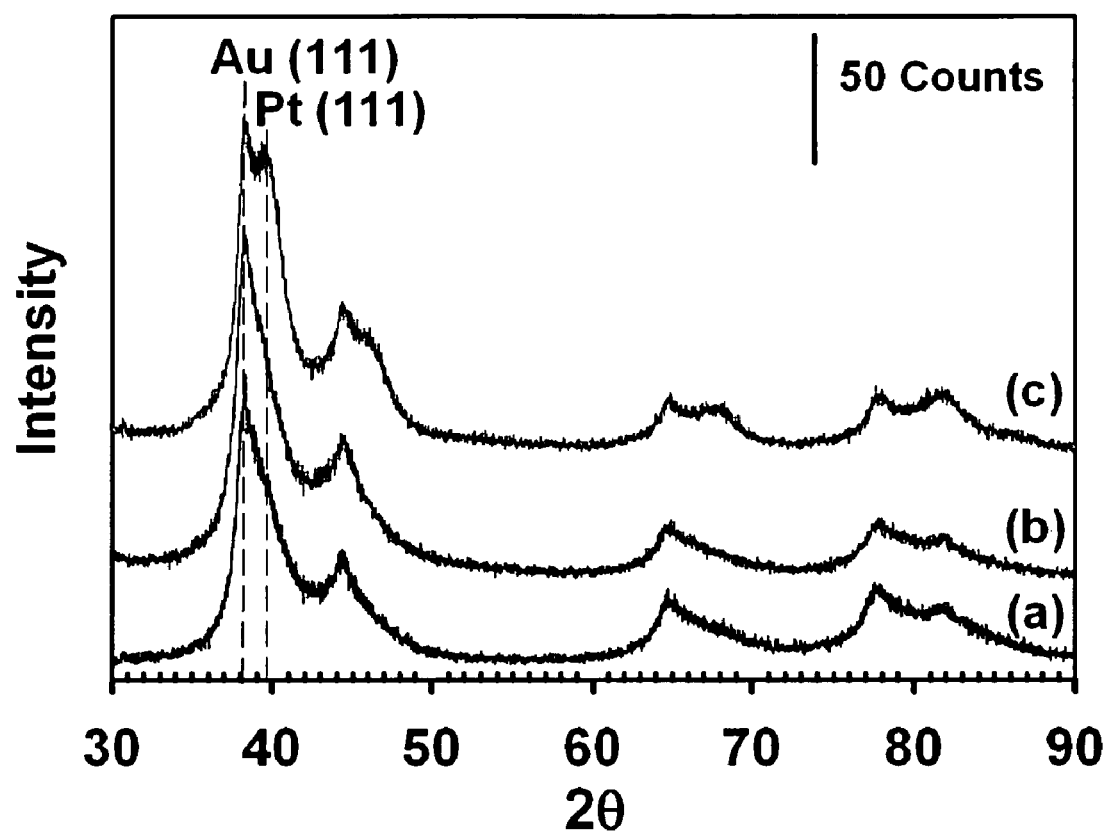
FIG. 13 shows X-ray diffractograms of untreated and thermally treated multiple shell particles.

In FIGS. 12a, 12b, the low contrast $Fe_3O_4$ is seen in FIG. 12a while the dark contrast in FIG. 12b shows the $Fe_3O_4$/Au/Pt particles. The $Fe_3O_4$/Au, $Fe_3O_4$/Pt, $Fe_3O_4$/Au/Pt and $Fe_3O_4$/Pt/Au nanoparticles can also be assembled on different supporting materials followed by thermal treatments. XRD data for a preliminary sample of thermally-treated $Fe_3O_4$/Au/Pt/C, as shown in FIG. 13, clearly showed phase-segregation for Pt and Au, which is in sharp contrast to the single-phase character found for some AuPt bimetallic nanoparticles. (FIG. 13 XRD for $Fe_3O_4$/Au/Pt/C catalyst before thermal treatment (a), after thermal treatment at 280° C. (b), and after thermal treatment at 500° C. (c).)

Figure 14A:
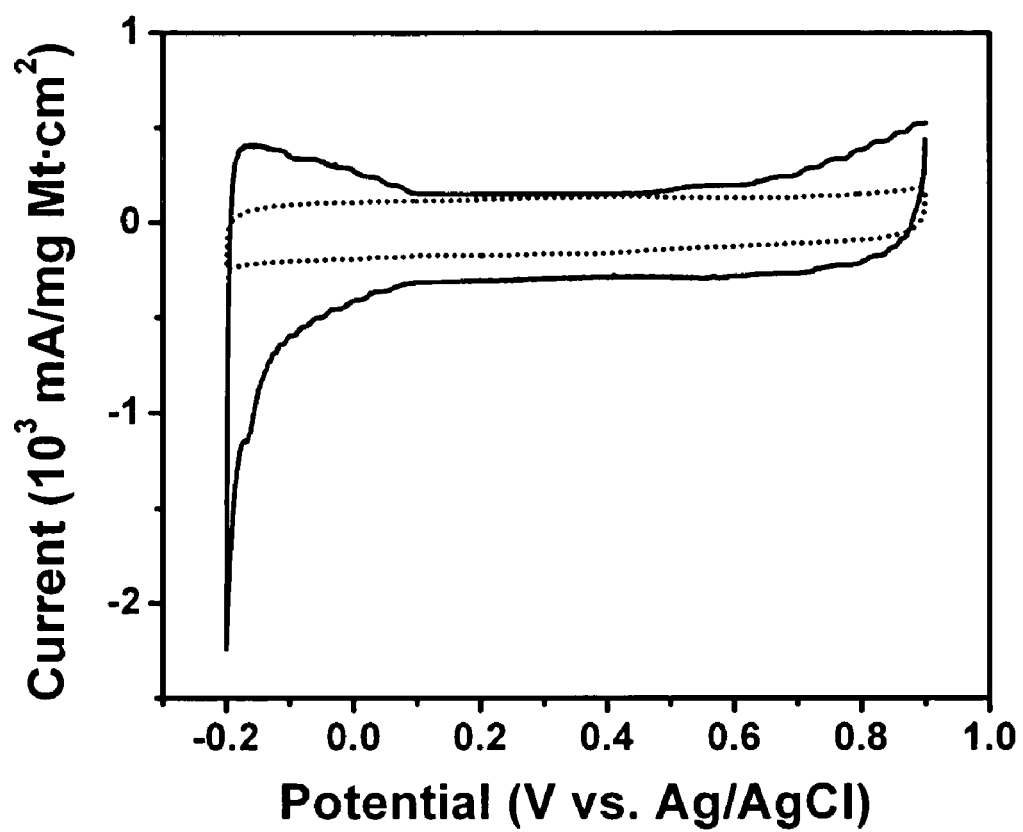
FIGS. 14a-14c show the reactivity in oxygen reduction reaction of single shell and multiple shell particles.
Figure 14B:
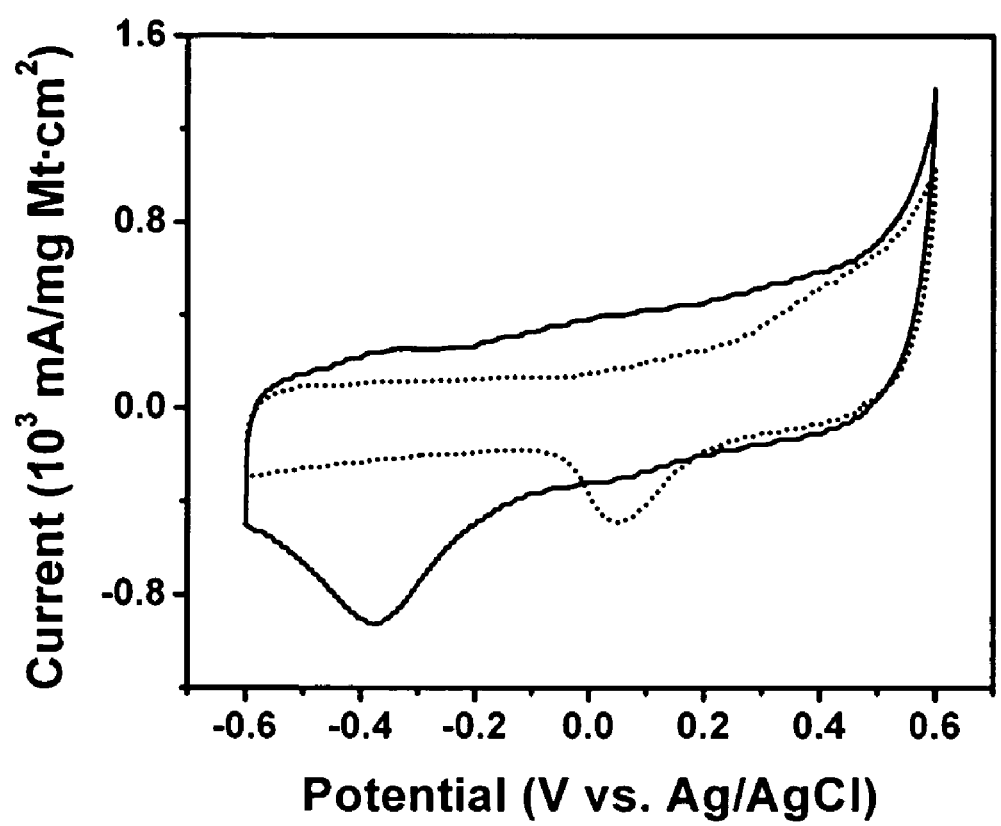
Figure 14C:
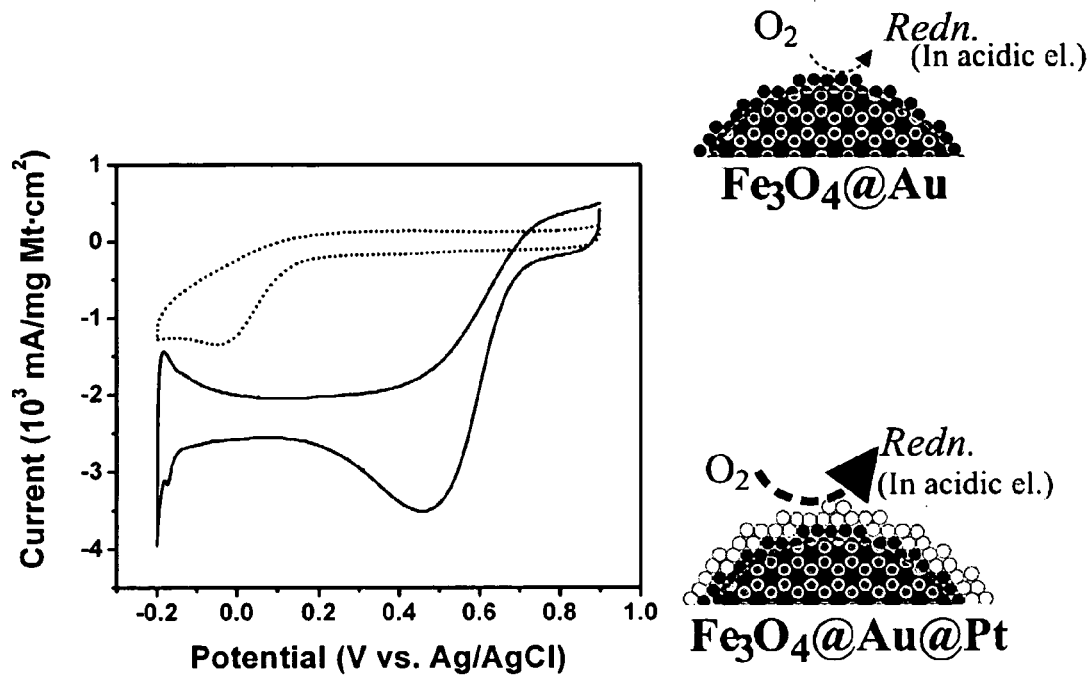

The detection of both Au and Pt and their phase segregation in the $Fe_3O_4$/Au/Pt sample is consistent with the core-shell structure by design, which is confirmed by other spectroscopic and electrochemical characterizations. FIGS. 14a-14c show the oxidation catalysis of the single and multi-shell particles differentiated by voltammetry for different electrolytes. CV curves for $Fe_3O_4$/Au (dotted curves) and $Fe_3O_4$/Au/Pt (solid curves) catalysts on GC electrode (0.2 cm$^2$) in $O_2$-free 0.5 M $H_2SO_4$ (FIG. 14a) and 0.5 M KOH (FIG. 14b) electrolytes, and in 0.5 M $H_2SO_4$ saturated with $O_2$. Scan rate: 50 mV/s (FIG. 14c). The graphic insert illustrates interfacial ORR (oxygen reduction reaction) reactivity.

The voltammetric measurements and Tafel analysis provides information for assessing the electrocatalytic methanol oxidation reaction (MOR) properties. FIG. 15 shows a preliminary set of results in which the potentials of oxygen reduction can be compared for $Fe_3O_4/Au/Pt/C$ and $Fe_3O_4/Au/C$.

Figure 15A:
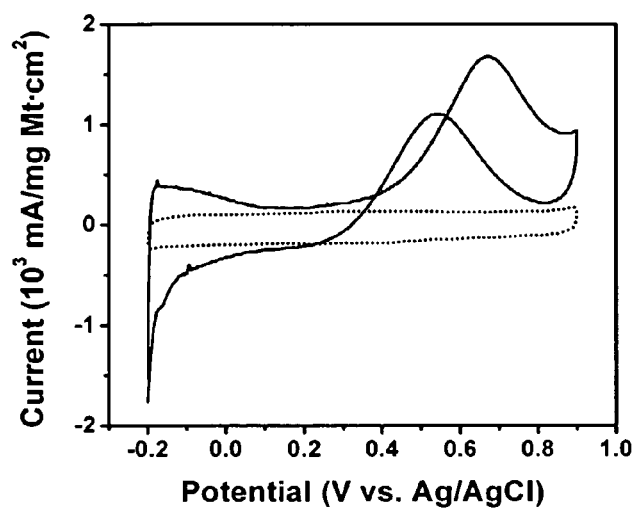
FIGS. 15a-15b show reactivity of single and multi-shell particles in MeOH oxidation reaction.
Figure 15A:
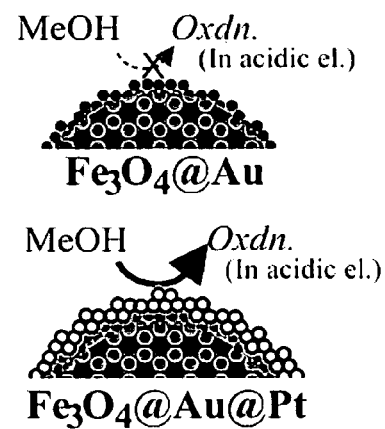
Figure 15B:
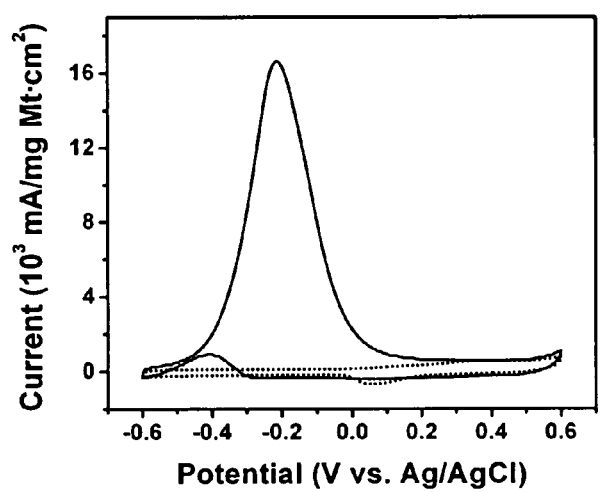
Figure 15B:
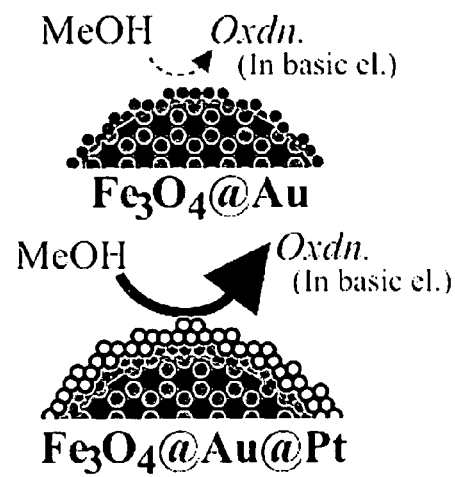

In FIGS. 15a, 15b, the CV curves for MOR: compares $Fe_3O_4/Au/C$ (dotted curves), and $Fe_3O_4/Au/Pt/C$ (solid curves) in 0.5 M $H_2SO_4$ (FIG. 15a) and 0.5 M KOH (FIG. 15b) electrolytes with 0.5 M MeOH (50 mV/s), respectively. The graphic inserts illustrate interfacial MOR reactivity of the two catalysts in the two electrolytes.

For both acidic and basic electrolytes, the MOR activity is evident for $Fe_3O_4/Au/Pt/C$ (solid curves), in contrast to the absence of activity in acidic electrolyte and low activity in basic electrolyte for $Fe_3O_4/Au/C$ (dotted curves). The catalytic activity higher than that for Pt/C catalysts in terms of current is remarkable. This is the first example demonstrating the effect of nanoscale oxide cores on the enhancement of Au and Pt catalytic activities.

In addition to $Fe_3O_4$, other Fe-Oxide nanoparticles or nanorods can also be used as the core materials. Examples include highly-crystalline $\gamma$-$Fe_2O_3$, $\alpha$-FeOOH, and $\beta$-FeOOH, some of which have been synthesized in the present inventor's laboratory. These are shown in FIGS. 11a-11f. TEM of the Fe-Oxide nanoparticles/nanorods shown include beta-FeOOH (FIG. 11A), $\alpha$-FeOOH (FIG. 11B), and $\gamma$-$Fe_2O_3$ (FIG. 11C), which can be used as the cores for the formation of the core/shell nanoparticles. In each case an HRTEM image is included.

A variety of reducing and oxidizing agents can be used for the synthesis, including the following exemplary compounds:
Reducing agents: polyols such as 1,2-hexadecanediol, ethylenediol.
Oxidizing agents: trimethylamine oxide dihydrate $((CH_1)_n NO \cdot 2H_2O)$, trimethylamine oxide $((CH_3)_3NO)$ and the like.

A variety of capping agents can be used for the synthesis, including, for example, R—$NH_2$, R—COOH, R—SH or polymers known to one of ordinary skill in the art, where R is an aromatic or aliphatic moiety.

Diverse solvents can be used for the synthesis, including aqueous and organic solvents, examples of the latter group including octyl ether, phenyl ether, ethylenediol.

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method of making mono-disperse iron oxide core metal shell (core/shell) nanoparticles comprising the steps of:
   a) reacting a suitable precursor compound of a superparamagnetic core material with one or more reactants in a solution containing first capping agents and a first solvent, thereby producing capped nanoparticle seeds in suspension;
   b) reacting the capped nanoparticle seeds in suspension with suitable metal precursor compounds and second capping agents in a second organic solvent, thereby producing polydisperse core/shell nanoparticles comprising a coarse fraction and a fine fraction;
   c) segregating a coarse fraction of the polydisperse core/shell nanoparticles and removing the coarse fraction in a first sizing operation; and
   d) further sizing the fine fraction, in a second sizing operation, to thereby produce mono-disperse core/shell nanoparticles.

2. The method of making core/shell nanoparticles according to claim 1, wherein the core material comprises an iron-oxide.

3. The method of making core/shell nanoparticles according to claim 2, wherein said suitable precursors to the superparamgnetic iron-oxide cores include Fe $(acac)_3$, Fe $(CO)_5$, $FeCl_2$, $FeCl_3$, and Fe $(acac)_2$.

4. The method of making core/shell nanoparticles according to claim 2, wherein the iron-oxide is selected from the group consisting of: $Fe_3O_4$, $\gamma$-$Fe_2O_3$, FeOOH, and $\alpha$-$Fe_2O_3$.

5. The method of making core/shell nanoparticles according to claim 2, wherein said iron oxide core comprises a superparamagnetic material.

6. The method of making core/shell nanoparticles according to claim 1, wherein the step (b) of reacting the capped nanoparticle seeds comprises:
   i) removing the first capping layer;
   ii) encapsulating the superparamagnetic core seed in a metal shell; and
   iii) capping the resultant core/shell nanoparticle with the second capping layer.

7. The method of making core/shell nanoparticles according to claim 6, wherein step (i) removing the first capping layer is accomplished by thermal desorption of the capping layer.

8. The method of making core/shell nanoparticles according to claim 1, wherein the shell metal precursor compounds comprise at least one compound selected from the group consisting of:
   Au $(acac)_3$, Au $(ac)_3$, $HAuCl_4$, Pt $(acac)_2$, $H_2PtCl_4$, TiO $(acac)_2$,
   VO $(acac)_2$, Fe $(acac)_3$, V $(acac)_3$, Co $(acac)_2$, Co $(acac)_3$, Ni $(acac)_2$, Ru $(acac)_3$, Cr$(acac)_3$, $MoO_2$, $(acac)_2$, Ta $(OC_2H_5)_4$ (acac),
   Zr $(acac)_4$, Mn $(acac)_2$, Mn $(acac)_3$, Fe $(acac)_2$, and Sn $(acac)_2$.

9. The method of making core/shell nanoparticles according to claim 1, wherein the shell material is selected from the group consisting of: Fe, Ni, Co, Mn, and alloys thereof and other metals and metalloids; inorganic compounds of metals such as oxides; and mixtures and solid solutions of the inorganic compounds.

10. The method of making core/shell nanoparticles according to claim 1, wherein said suitable precursors to the cores include iron acetyl acetonates, carbonates and chlorides.

11. A method of making core/shell nanoparticles comprising the steps of:
   a) reacting Fe $(acac)_3$, in phenyl ether in the presence of 1,2-hexadecanediol, oleic acid, oleylamine, thereby producing oleic acid and oleylamine capped $Fe_3O_4$ nanoparticle seeds in suspension;
   b) reacting the capped $Fe_3O_4$ nanoparticle seeds in suspension with Au $(OOCCH_3)_3$ and phenyl ether in the presence of 1,2-hexadecanediol, oleic acid and oleylamine, to thereby produce polydisperse core/shell nanoparticles comprising a coarse fraction and a fine fraction, wherein each core/shell nanoparticle comprises an $Fe_3O_4$ core enclosed in an Au-shell further covered by an oleylamine capping layer;
   c) segregating a coarse fraction of the polydisperse core/shell nanoparticles and removing the coarse fraction in a first sizing operation; and d) further sizing the fine fraction, in a second sizing operation, to thereby produce mono-disperse core/shell nanoparticles.

12. The method of making core/shell nanoparticles according to claim 11, wherein the step (b) of reacting the capped $Fe_3O_4$ nanoparticle seeds comprises:
   removing the first oleic acid and oleylamine capping layer;
   enclosing a superparamagnetic core seed in a metal shell; and
   capping the resultant core/shell nanoparticle with the second capping layer.

13. The method of making core/shell nanoparticles according to claim 12, wherein removing the first capping layer is accomplished by thermal desorption of the capping layer.

14. The method of making core/shell nanoparticles according to claim 12, wherein the second capping layer comprises oleic acid and oleylamine.

15. The method of making core/shell nanoparticles according to claim 12, wherein the second capping layer comprises an organic compound of the general formula selected from the group consisting of: R—$NH_2$, R—COOH, and R—SH, where R is a functional moiety selected from the group consisting of aliphatic and aromatic groups.

16. The method of making core/shell nanoparticles according to claim 12, wherein the second capping layer is a polymer.

17. The method of making core/shell nanoparticles according to claim 11, wherein the first and second sizing operations comprise centrifuging the suspension at a first speed and removing the first settled fraction of particles followed by centrifuging at a second speed and removing the second settled fraction of particles.

18. The method of making core/shell nanoparticles according to claim 17, wherein the second speed is greater than the first speed.

19. The method of making core/shell nanoparticles according to claim 11, characterized in that the coarse fraction comprises core/shell nanoparticles having diameters in the range 5-90 nm with a standard deviation of 0.1-5.4 nm.

20. The method of making core/shell nanoparticles according to claim 11, characterized in that the fine fraction comprises core/shell nanoparticles having diameters in the range 5-50 nm.

21. The method of making core/shell nanoparticles according to claim 20, wherein the fine fraction core/shell nanoparticles are mono-disperse having a narrow size distribution with a standard deviation typically in the range 0.2-2.5 nm.

22. The method of making core/shell nanoparticles according to claim 20, wherein the mean diameter of a superparamagnetic core seed can be selected to lie in the range 2.0-50.0 nm.

23. The method of making core/shell nanoparticles according to claim 20, wherein the diameter of the superparamagnetic core seed has a narrow dispersion characterized by a standard deviation in the range 0.1-2.5 nm.

24. The method of making core/shell nanoparticles according to claim 11, wherein the thickness of the gold shell is varied with the seed dimension according to the relation:

$$d = \frac{D}{2} \times (\sqrt[3]{0.6858 \times AR} + 1 - 1)$$

where d=shell thickness;
D=diameter of core seed; and
AR=atomic weight ratio of Au/Fe.

25. A method of forming a self-assembled thin film layer of $Fe_3O_4$/Au core/shell nanoparticles on a substrate, comprising the steps of:
   a) reacting Fe (acac)$_3$ and phenyl ether in the presence of 1,2-hexadecanediol, oleic acid and oleylamine, thereby producing oleylamine capped $Fe_3O_4$ nanoparticle seeds in suspension;
   b) reacting the capped $Fe_3O_4$ nanoparticle seeds in suspension with Au $(OOCCH_3)_3$ and phenyl ether in the presence of 1,2-hexadecanediol, oleic acid, oleylamine, to thereby produce polydisperse core/shell nanoparticles comprising a coarse fraction and a fine fraction;
   c) segregating a coarse fraction of the polydisperse core/shell nanoparticles and removing the coarse fraction in a first sizing operation;
   d) further sizing the fine fraction in a second sizing operation and removing the fine fraction, to thereby produce mono-disperse core/shell nanoparticles comprising a $Fe_3O_4$ core enclosed in a Au shell further covered by an oleylamine capping layer;
   e) mixing the core/shell nanoparticles from step (d) with NDT (1,9-nonanedithiol) or MUA (mercaptoundecanoic acid) in hexane forming a thiol-mediated core/shell nanoparticle suspension; and
   f) immersing the substrate in the thiol-mediated core/shell nanoparticle suspension and forming at least one thin film layer of core/shell nanoparticles.

26. A method of making mono-disperse iron-oxide core metal shell (core/multi-shell) nanoparticle composites comprising the steps of:
   a) reacting a suitable precursor compound of the iron-oxide core material with at least one reactant in a solution containing first capping agents and a first solvent, thereby producing capped nanoparticle seeds in suspension;
   b) reacting the capped nanoparticle seeds in suspension with suitable first-metal precursor compounds and second capping agents in a second organic solvent, thereby producing core/first-shell nanoparticles;
   c) further reacting the core/first-shell nanoparticles in suspension with suitable second-metal precursor compounds and third capping agents in a third organic solvent, thereby producing core/multi-shell nanoparticle composites comprising a coarse fraction and a fine fraction;
   d) segregating a coarse fraction of the polydisperse core/multi-shell nanoparticle composites and removing the coarse fraction in a first sizing operation; and
   e) further sizing the fine fraction, in a second sizing operation, to thereby produce mono-disperse core/multi-shell nanoparticle composites.

27. The method of making mono-disperse core/metal shells (core/multi-shell) nanoparticle composites according to claim 26, wherein the first shell ($T_1$) is Au and the second shell ($T_2$) is Pt.

28. The method of making core/shell nanoparticles according to claim 27, wherein the temperature of reaction for the second shell ($T_2$) is greater than the temperature of reaction for the first shell ($T_1$).

29. The method of making core/multi-shell nanoparticle composites according to claim 26, wherein the first shell ($T_1$) is Pt and the second shell ($T_2$) is Au.

* * * * *